United States Patent
Calderon et al.

(10) Patent No.: US 7,920,910 B2
(45) Date of Patent: Apr. 5, 2011

(54) SYSTEM, METHOD AND APPARATUS FOR SURGICAL PATIENT TABLE

(75) Inventors: Paul David Calderon, Castro Valley, CA (US); Travis Roy Monke, Shorewood, WI (US); Yoram Goren, Hod-Hasharon (IL); Amiel Grinberg, Haifa (IL)

(73) Assignee: General Electric Company, Schenectady, NY (US)

( * ) Notice: Subject to any disclaimer, the term of this patent is extended or adjusted under 35 U.S.C. 154(b) by 209 days.

(21) Appl. No.: 12/269,536

(22) Filed: Nov. 12, 2008

(65) Prior Publication Data
US 2009/0056023 A1 Mar. 5, 2009

Related U.S. Application Data

(62) Division of application No. 11/127,363, filed on May 12, 2005, now Pat. No. 7,467,004.

(51) Int. Cl.
*A61B 5/05* (2006.01)
*A47B 71/00* (2006.01)
*A47B 13/00* (2006.01)

(52) U.S. Cl. ................. 600/415; 5/600; 5/601
(58) Field of Classification Search .......... 600/415; 5/600–601
See application file for complete search history.

(56) References Cited

U.S. PATENT DOCUMENTS

| | | | |
|---|---|---|---|
| 4,105,923 A | 8/1978 | Hynes, Jr. | |
| 4,475,072 A | 10/1984 | Schwehr et al. | |
| 4,641,823 A | 2/1987 | Bergman | |
| 4,671,728 A | 6/1987 | Clark et al. | |
| 4,891,851 A | 1/1990 | Sierocuk et al. | |
| 5,083,331 A | 1/1992 | Schnelle et al. | |
| 5,123,797 A | 6/1992 | Schnelle et al. | |
| 5,154,562 A | 10/1992 | Dornauer | |
| 5,197,474 A | 3/1993 | Englund et al. | |
| 5,475,884 A | 12/1995 | Kirmse et al. | |
| 5,513,406 A | 5/1996 | Foster et al. | |
| 5,551,430 A | 9/1996 | Blakeley et al. | |

(Continued)

FOREIGN PATENT DOCUMENTS

| | | |
|---|---|---|
| EP | 0857458 B1 | 8/1998 |
| GB | 2394412 A1 | 4/2004 |

OTHER PUBLICATIONS

Internet Citing: "Neurovascular XMR Suite and Patient Transport System for the Clinical Treatment of Acute Stroke and other Neurovascular Diseases: Initial Clinical Experience"[online]; [Retrieved on Feb. 12, 2009]; retrieved from the Internet: http://radiologie.uniklinikum-leipzig.de/start/archiv/5thinterventional/Abstracts%20ORAL/SESSION%206%20TECHNICAL%20SYSTEMS/602%20Neurovascular%20XMR%20Suite%20and%20Patient%20Transport%20System.pdf.

(Continued)

*Primary Examiner* — Long V Le
*Assistant Examiner* — Michael T Rozanski
(74) *Attorney, Agent, or Firm* — Cantor Colburn LLP

(57) ABSTRACT

A patient table includes a cradle for slidably receiving a board carrying a patient, a cradle supporting member for slidably receiving the cradle, a locker for preventing the board from sliding off the cradle, and a stopper for preventing the cradle from sliding off the cradle supporting member. A method of transferring a patient to an imaging system from a second table uses the patient table to move the board from the second table to the patient table to the imaging system. An RF coil system usable with the table includes a coil, a coil cable, an intermediate box for receiving the coil cable, and a system cable extending from the intermediate box and connected to the imaging system.

5 Claims, 20 Drawing Sheets

U.S. PATENT DOCUMENTS

| | | |
|---|---|---|
| 5,651,150 A | 7/1997 | Kanitzer et al. |
| 5,842,987 A | 12/1998 | Sahadevan |
| 6,322,251 B1 | 11/2001 | Ballhaus et al. |
| 6,389,623 B1 | 5/2002 | Flynn et al. |
| 6,640,364 B1 | 11/2003 | Josephson et al. |
| 6,782,571 B1 | 8/2004 | Josephson et al. |
| 6,928,672 B2 | 8/2005 | Pastyr et al. |
| 7,010,085 B2 | 3/2006 | Kroner et al. |

OTHER PUBLICATIONS

Internet Citing: "Magnetic Resonance Imaging"[online], retrieved on Apr. 25, 2007]; retrieved from the Internet: http://www.gehealthcare.comicgi-bin/print/print.cgi.

Internet Citing: "Company News"[online]; [retrieved on Apr. 25, 2007]; retrieved from Internet: http://www.gehealthcare.com/cgi-bin/print/print.cgi.

Netherlands Search Report for Application No. 1031753 [3 pgs.].

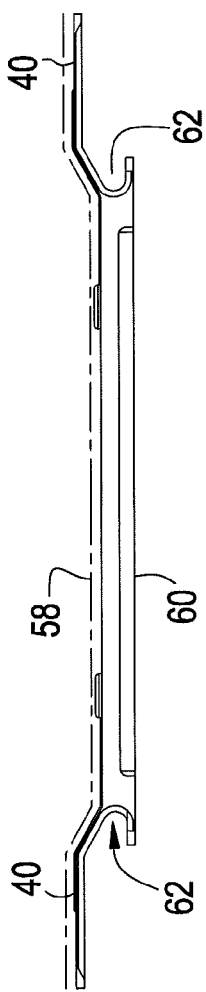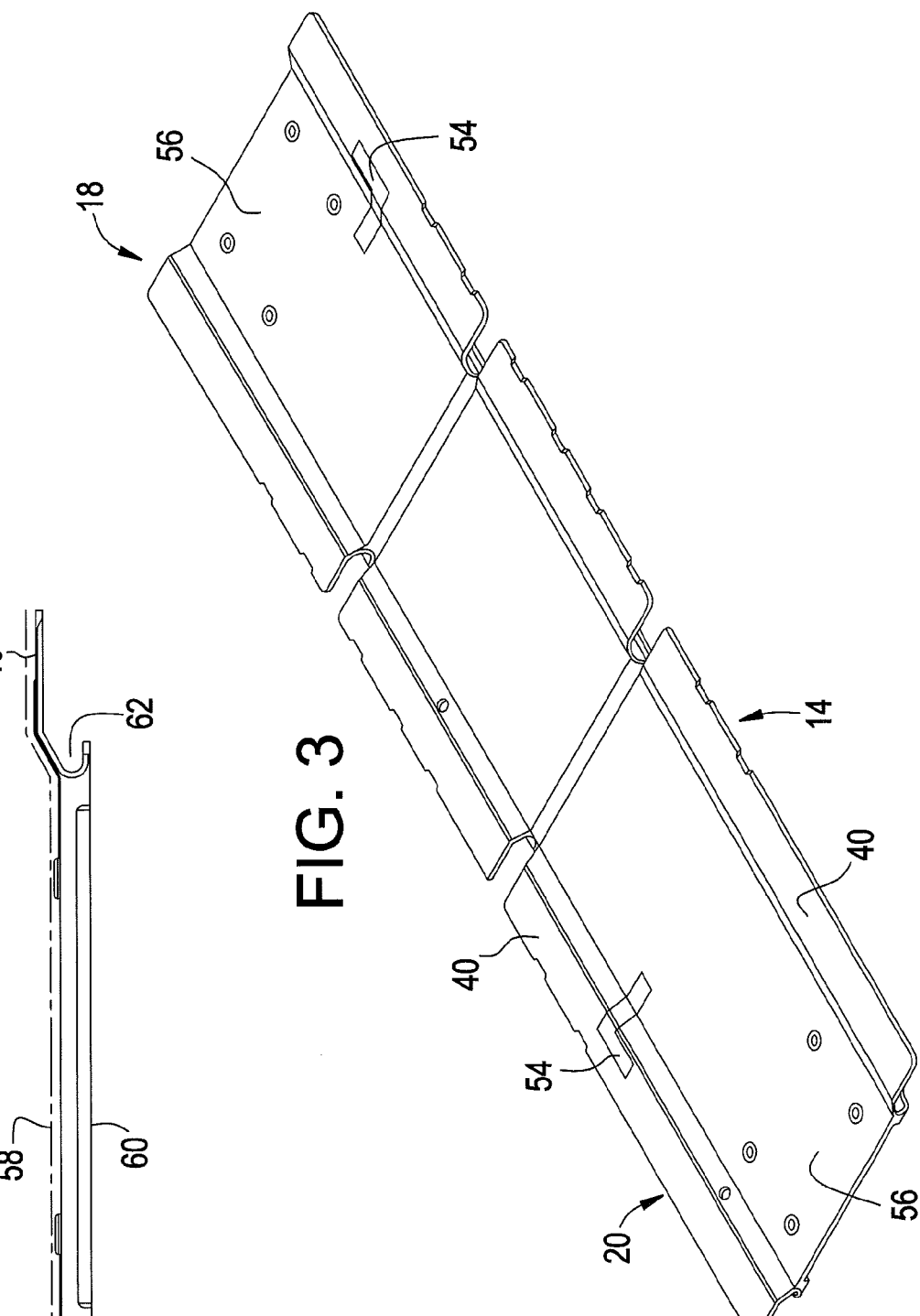

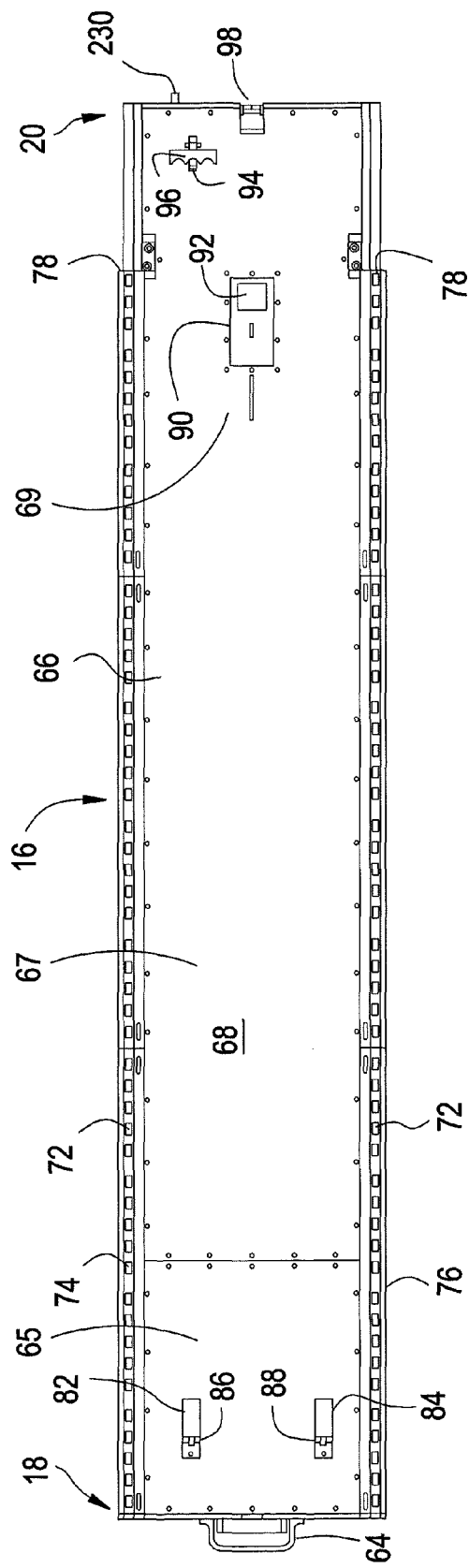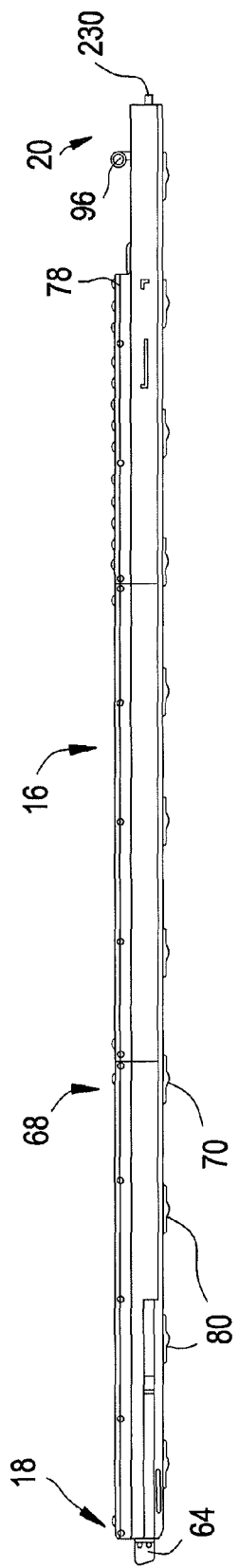

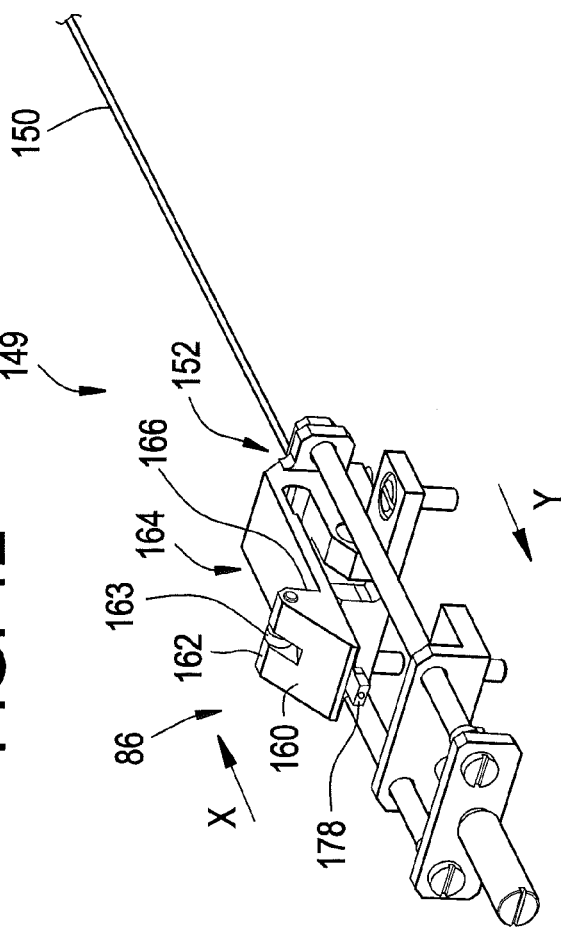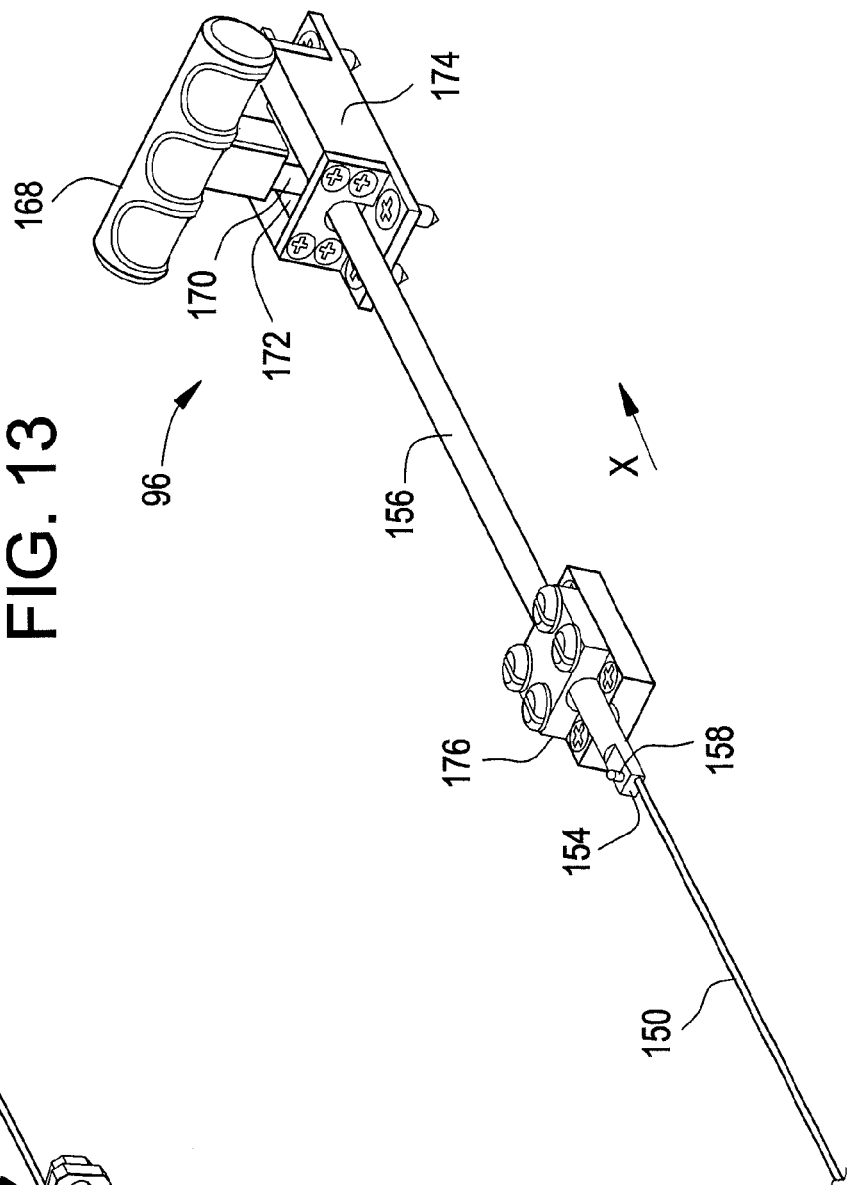

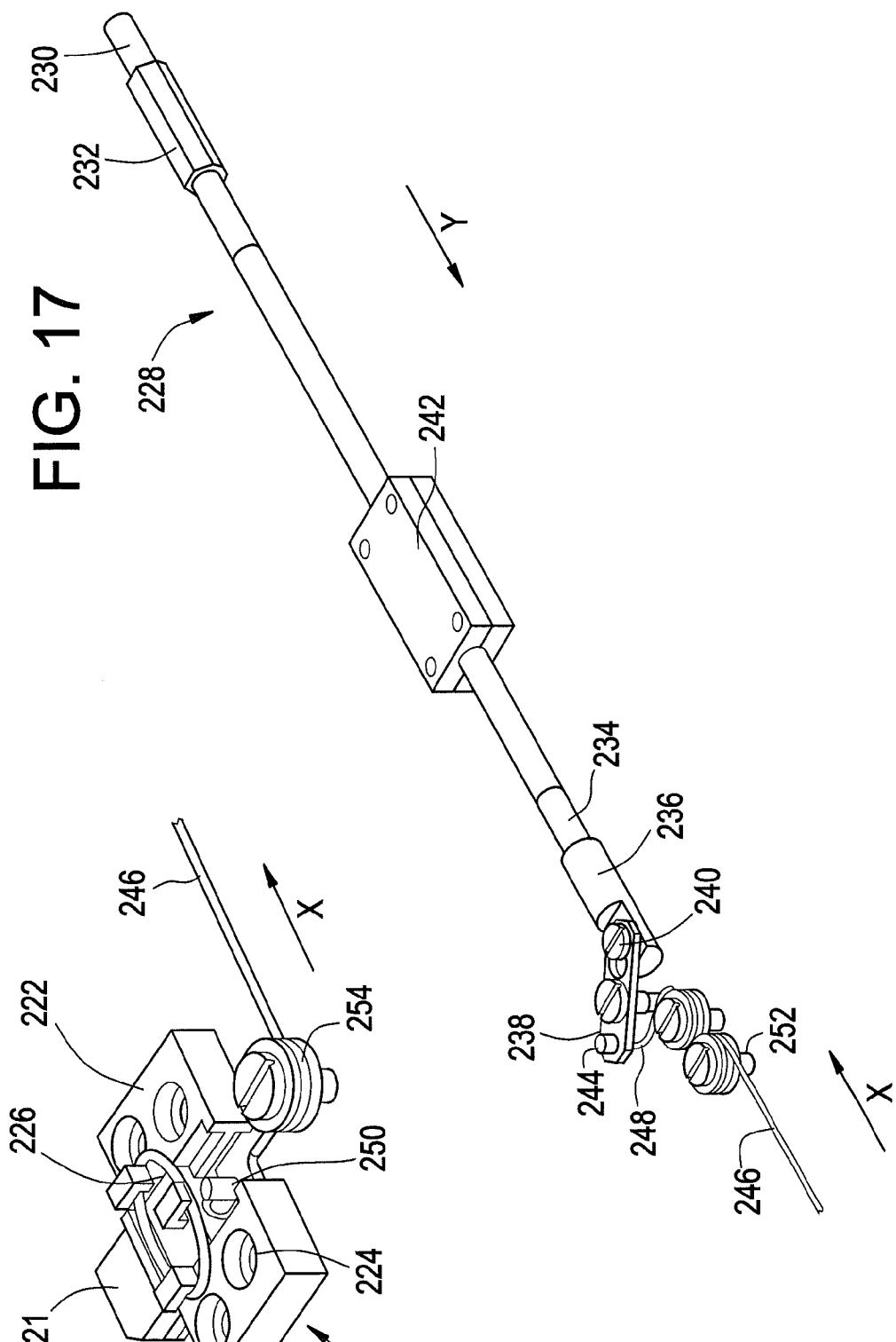

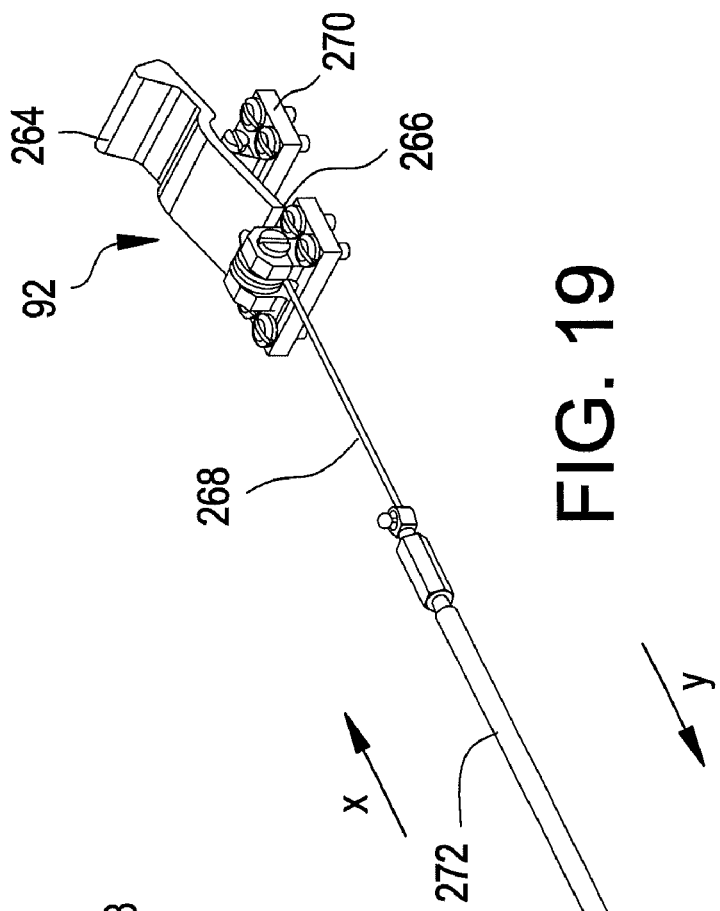
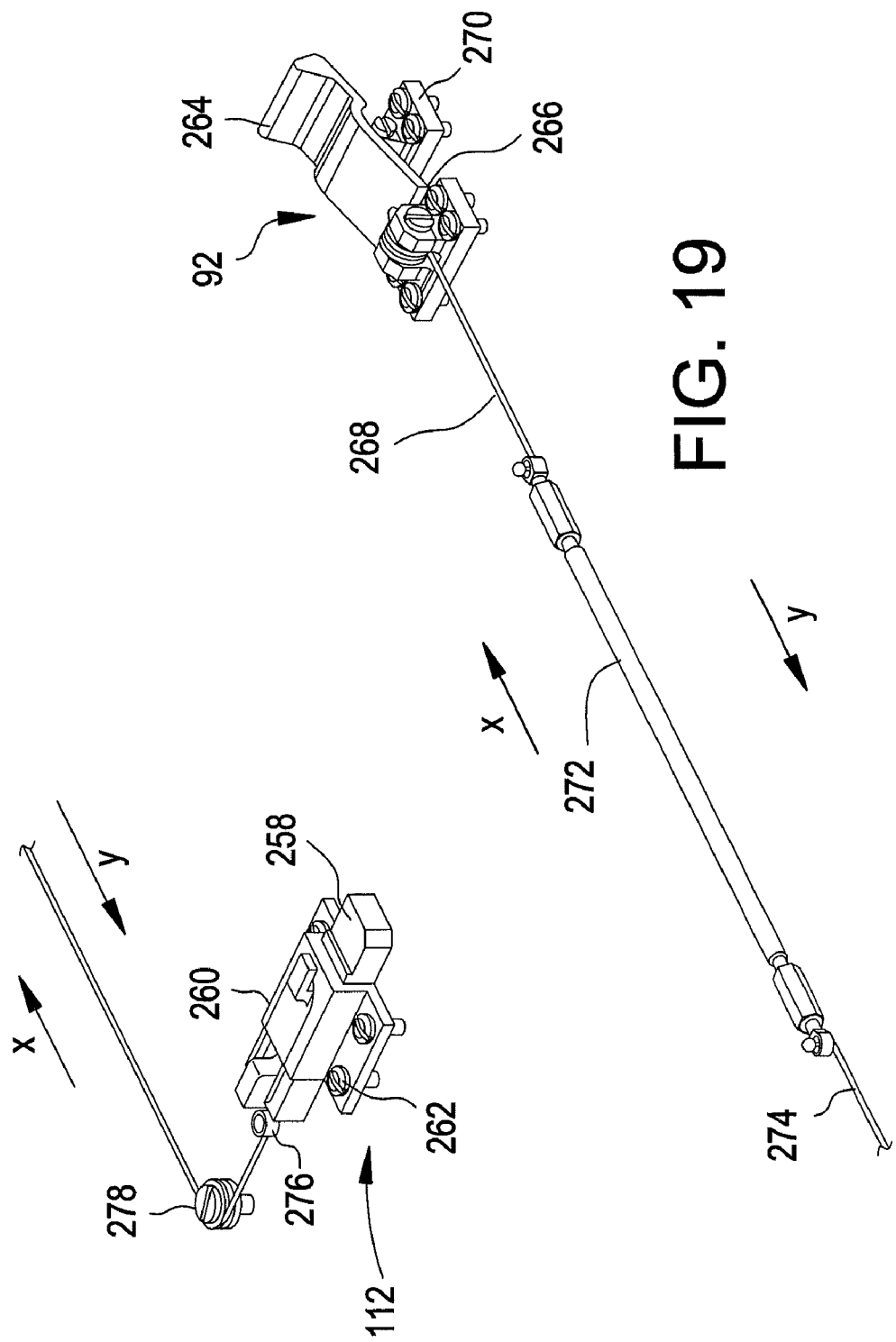

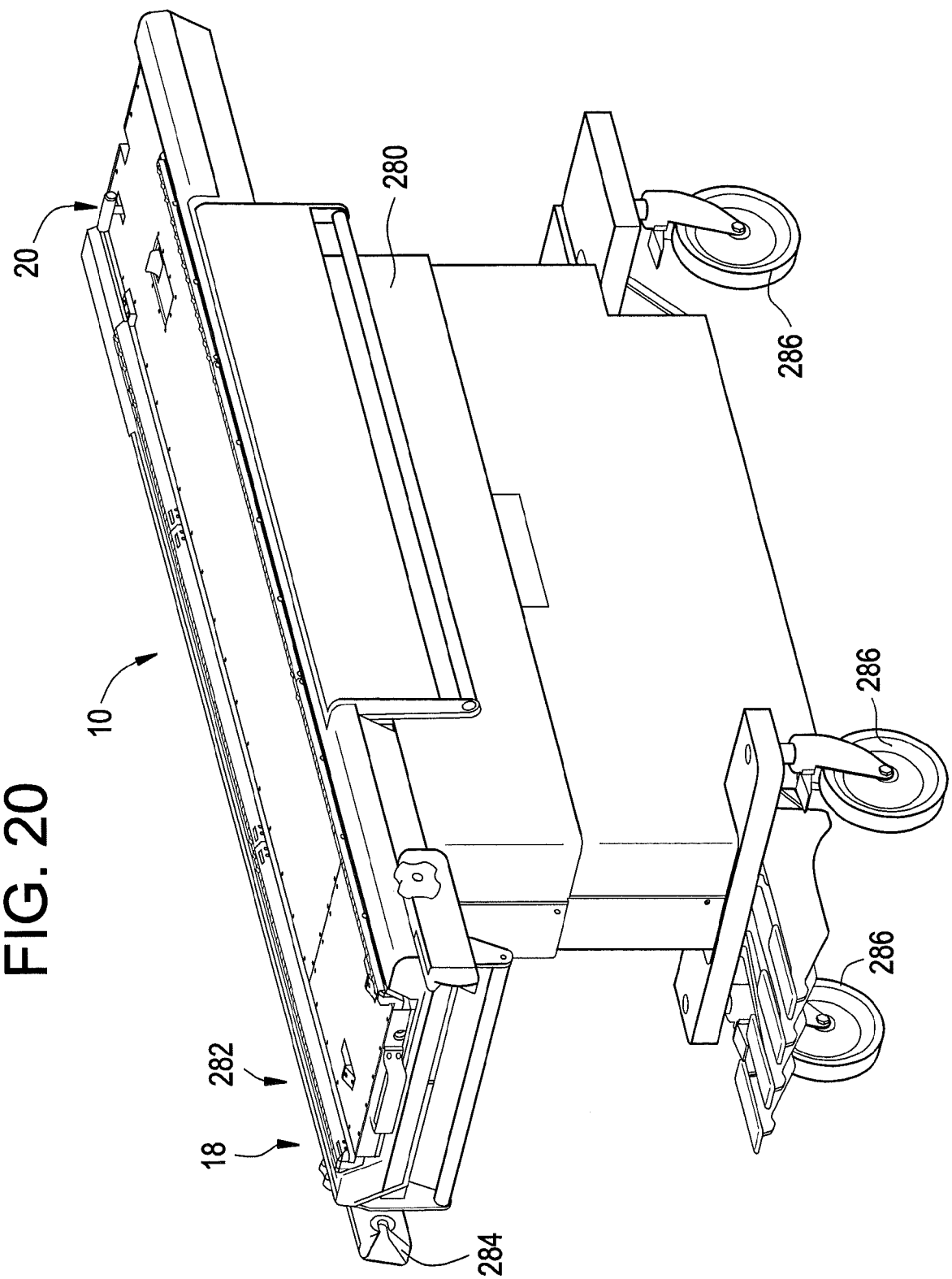

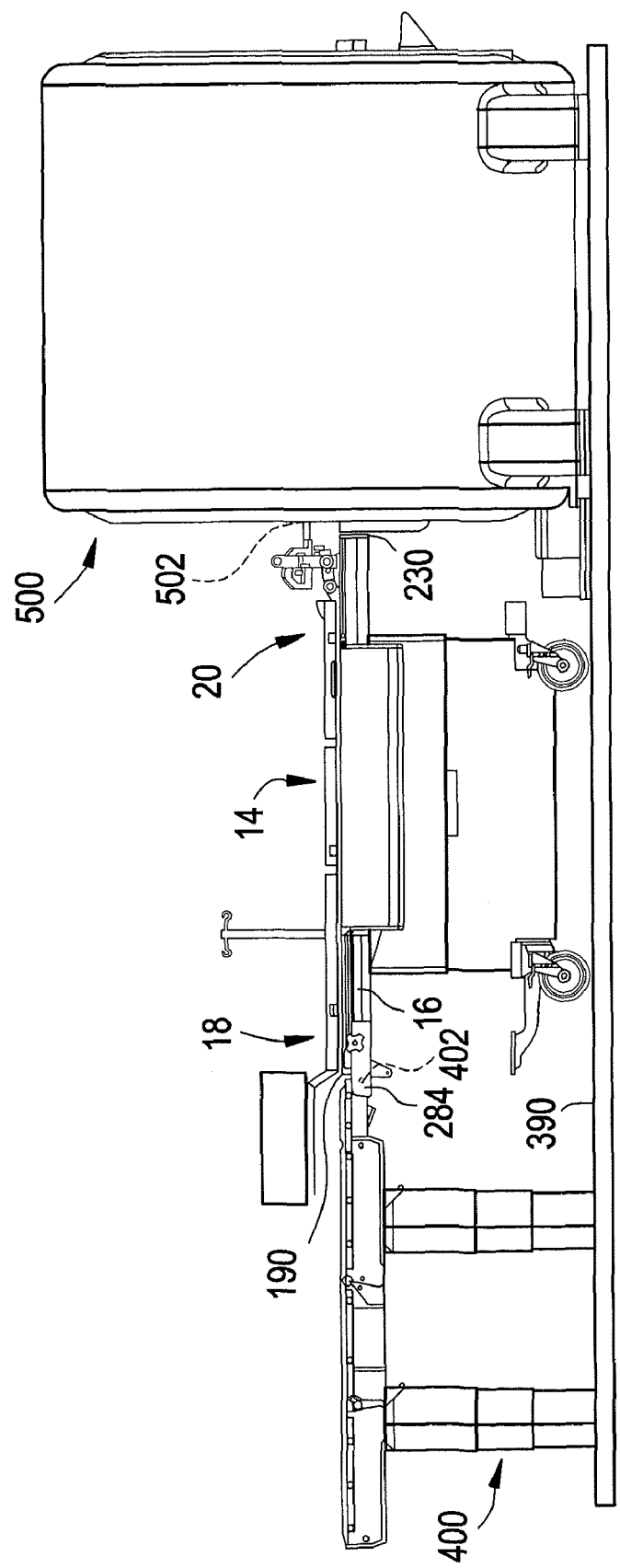

SYSTEM, METHOD AND APPARATUS FOR SURGICAL PATIENT TABLE

CROSS REFERENCE TO RELATED APPLICATIONS

This application is a divisional application of U.S. application Ser. No. 11/127,363 filed May 12, 2005, which is hereby incorporated by reference in its entirety.

BACKGROUND OF THE INVENTION

This application relates to a patient table. More particularly, this application relates to a patient table for transferring a patient from a second table into an imaging system.

Currently, patients and objects can be imaged using a wide variety of different imaging technologies. Such imaging technologies can include MRI, computer tomography ("CT"), x-ray imaging, and others. Each imaging technology has unique advantages and disadvantages in imaging certain types of physiological or physical characteristics. MRI images, for example, provide excellent soft tissue contrast with no exposure to ionizing radiation. MRI images also provide three-dimensional image acquisition.

MRI is a diagnostic imaging modality that does not rely on ionizing radiation. Instead, it uses strong (ideally) static magnetic fields, RF pulses of energy and magnetic field gradient waveforms. An RF coil produces the RF pulses. MRI is a non-invasive procedure that uses nuclear magnetization and radio waves for producing internal pictures of a subject. Three-dimensional diagnostic image data is acquired for respective "slices" of an area of the subject under investigation. These slices of data typically provide structural detail having a resolution of one millimeter or better. An MRI system requires not only an intensive uniform magnetic field generator, but also a suite of associated electronics to operate the MRI system.

For a surgical operating room ("OR") situation, patient transfer from surgery into a MRI scanner during a surgical procedure has only been available if the patient is physically lifted from the OR table, which involves extreme risk to the patient. Such a procedure can cause excessive anatomical movement and disruption of the patient.

BRIEF DESCRIPTION OF THE INVENTION

Exemplary embodiments of the invention include a patient table including a cradle for linearly receiving and transferring a board carrying a patient, a cradle supporting member for slidably receiving the cradle, a locker within the cradle for positioning the board and patient on the table, and for preventing the board from sliding off the cradle, and a stopper within the cradle for preventing the cradle from sliding off the cradle supporting member.

Further exemplary embodiments of the invention include a method of transferring a patient to an imaging system, the method including docking a first end of a patient table with a second table, sliding a patient carrying board from the second table over a cradle of the patient table, wherein the board automatically locks onto the cradle when in place on the cradle, moving a second end of the patient table into engagement with the imaging system, wherein the cradle is unlocked from a cradle supporting member of the patient table when the second end of the patient table is engaged with the imaging system, and moving the cradle and board into the imaging system.

Still further exemplary embodiments of the invention include a patient imaging and transfer system, the system including an imaging system, a patient table including a cradle supporting member, a second end of the table engageable with the imaging system, a cradle slidably received on the cradle supporting member and within the imaging system, the cradle movable between the patient table and the imaging system when the second end of the table is engaged with the imaging system, a second table, an end of the second table engageable with a first end of the patient table, and a patient carrying board slidable between the second table and the cradle when the second table is engaged with the first end of the patient table, wherein a patient is transferable from the second table to the imaging system without removing the patient from the board.

Yet further exemplary embodiments of the invention include an RF coil system including a coil, a coil cable extending from the coil, an intermediate box for receiving the coil cable, the intermediate box attachable to a patient carrying board, and a system cable extending from the intermediate box, the system cable connectable to an imaging system, wherein the RF coil system is positioned relative to a patient carrying board, and movable with a patient carrying board towards and away from the imaging system, and wherein the RF coil system is connectable with an imaging system using a single connection between the system cable and the imaging system.

The above, and other objects, features and advantages of the present invention will become apparent from the following description read in conjunction with the accompanying drawings, in which like reference numerals designate the same elements.

BRIEF DESCRIPTION OF THE DRAWINGS

Referring now to the drawings wherein like elements are numbered alike in the several FIGURES:

FIG. 3 shows a side perspective view of an exemplary embodiment of the patient carrying board for use with the patient table of FIG. 1;

FIG. 4 shows an end cross-sectional view of the patient carrying board of FIG. 3;

FIG. 6 shows a top plan view of the cradle of FIG. 5;

FIG. 7 shows a side plan view of the cradle of FIG. 5;

FIG. 12 shows a side perspective view of a portion of an exemplary embodiment of a locker manual release mechanism for use with the table of FIG. 1;

FIG. 13 shows a side perspective view of another portion of the locker manual release mechanism of FIG. 12;

FIG. 16 shows a side perspective view of a portion of an exemplary embodiment of a first stopper for the table of FIG. 1;

FIG. 17 shows a side perspective view of another portion of the first stopper of FIG. 16;

FIG. 18 shows a side perspective view of a portion of an exemplary embodiment of a second stopper for the table of FIG. 1;

FIG. 19 shows a side perspective view of another portion of the second stopper of FIG. 18;

FIG. 20 shows a side perspective view of the patient table of FIG. 1;

FIG. 25 shows a schematic view of an exemplary embodiment of an overall system for patient transference and imaging using the table of FIG. 1.

DETAILED DESCRIPTION OF THE INVENTION

The exemplary embodiments of systems, methods, and devices described herein enable smooth and safe patient transfer and provide imaging capability utilizing RF coils.

As will be further described below, the systems and devices described herein include a combined integration of multiple modalities and may utilize an established OR surgical table device as a second table known as Vascular Interventional Workplace for Advanced Surgery ("VIWAS") provided by Maquet Company. The common link for all the equipment described herein is a surgical work surface such as a fiber composite transfer board for patient positioning/resting. This transfer board, with patient, can be used for surgery in an OR situation. A track system can then be used to move the patient to/from the OR and imaging system, such as the MR scanner. Utilizing this transfer board as the platform as an interface between both devices, the embodiments described herein include a surgical patient table that accepts the transfer board onto a unique table cradle and docking the patient table with an imaging system, such as, but not limited to, a GE Signa scanner, available from General Electric. The surgical patient table is configured to connect/interface with a second table such as, but not limited to, the Maquet VIWAS and also Maquet's patient transporter (known as Transmobile). As will be further described, safety interlocks are included within the cradle to permit safe, smooth patient transfer.

As part of the embodiments described herein, a method for imaging is provided to facilitate utilization of a coil, such as an RF coil, with surgical procedures. The RF coil implementation enables positioning of the coil between an anatomical clamp, such as a skull clamp, and the patient's anatomy, such as the head, to maximize a signal-to-noise ratio ("SNR") and ease positioning of a coil connection for the user. Although the coil will be described in the illustrated embodiment as usable with respect to the patient's head, other implementations would be within the scope of this method. SNR is the ratio of the magnitude of the wanted signal to that of the unwanted noise, expressed as a simple arithmetic ratio or in decibels. The coil interface configuration enables connection of the coil to an intermediate connection location for maximum flexibility in applications and procedures. The implementation can be connected to the transfer board on a patient's left or right side and the coil enables the use of a posterior coil, an anterior coil, or both used in conjunction. This capability allows for maximum user/application flexibility to accommodate the particular procedure.

Figure 1:
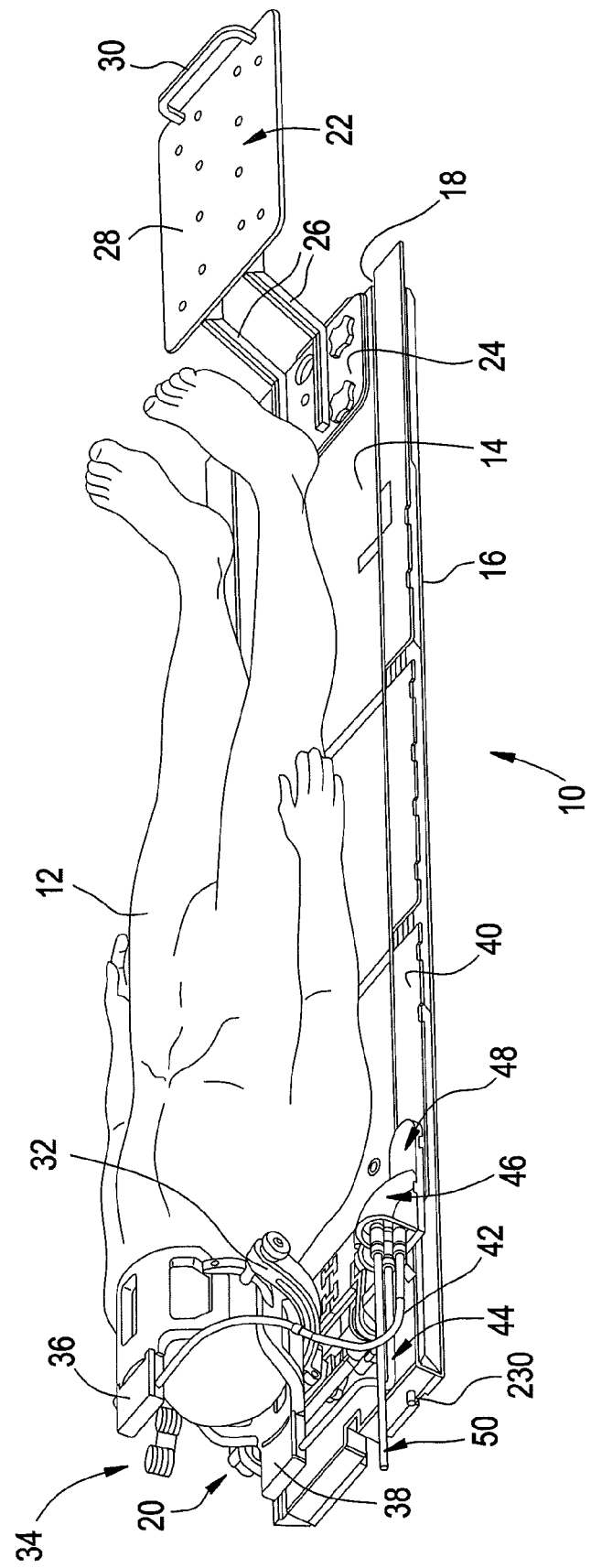
FIG. 1 shows a side perspective view of a portion of an exemplary embodiment of a patient table carrying a patient carrying board, a cradle, an RF coil system, and a patient.

Turning now to FIG. 1, an overall view of an exemplary embodiment of the table system 10 is shown. A patient 12 rests on the transfer board 14. The transfer board 14 is shown overlying and engaged with a cradle 16. The transfer board 14 and the cradle 16 are interconnected for movement within an imaging system, such as an MRI bore of an MRI system. The table 10 includes a first end 18 and a second end 20, that relate to a first end 18 and second end 20 of the transfer board 14 and cradle 16. The transfer board 14 includes side portions 40 that extend generally from the second end 20 to the first end 18. The patient 12 lies between the side portions 40. A patient's head would lie adjacent the second end 20, while the patient's feet would be positioned closer to the first end 18, although an opposite configuration is also within the scope of this table. A monitor plate 22 can be attached to the first end 18 of the transfer board 14. The monitor plate 22 can hold a monitor (not shown) for displaying patient vital signs (such as, but not limited to, ECG). The monitor can also be used for any other implementation deemed necessary by the user. The monitor plate 22, in the illustrated embodiment, includes an attachment plate 24 for attaching to the transfer board 14 and a pair of arms 26 extending towards a monitoring holding portion 28. A handle 30 may further be provided on the monitoring holding portion 28 for moving either the entire patient table 10 or adjusting positioning of the monitor plate 22.

The second end 20 of the transfer board 14 is shown outfitted with a clamp 32 for holding a patient's head therein. In the illustrated embodiment, an RF coil 34 is positioned between the clamp 32 and the patient's head. The coil 34 may be positioned on the patient in a variety of orientations and positions as defined by the procedure being done and as determined by the clinicians. The coil may be fixed to the skull clamp and/or patient using methods such as and not limited to Velcro strips, tape, or other method to secure the coil in place. The RF coil 34 includes either one or both of an anterior flex coil 36 and a posterior flex coil 38. It should be understood that while an exemplary arrangement of the RF coil 34 is shown, the coil 34 may also be utilized on different parts of the patient's anatomy, and therefore may include alternately designed coil sections. An anterior flex coil cable 42 extends from the anterior flex coil 36 and a posterior flex coil cable 44 extends from the posterior flex coil 38. The cables 42 and 44 include all of the necessary electrical and signaling connections for proper functioning of the coils 36 and 38. The cables 42 and 44 extend towards and connect to an intermediate box 46. The cables 42 and 44 may be detachable from the intermediate box 46 for removal of a particular coil 36 or 38 from the table 10. The intermediate box may be sized for connecting to more or less coil cables as desired. The intermediate box 46 is attached to a side portion 40 of the transfer board 14 via an intermediate box extension arm 48. Extending from the intermediate box 46 is a system cable 50. The system cable 50 is connectable with an MR system coil interface 502, as shown in FIG. 25. The system cable 50 enables the table 10 to have a "plug and go" MRI-ready connection, as there is only one cable connection, cable 50, that needs to be connected to the MRI system coil when the table 10 is pushed into engagement with the MRI system 500.

Figure 2:
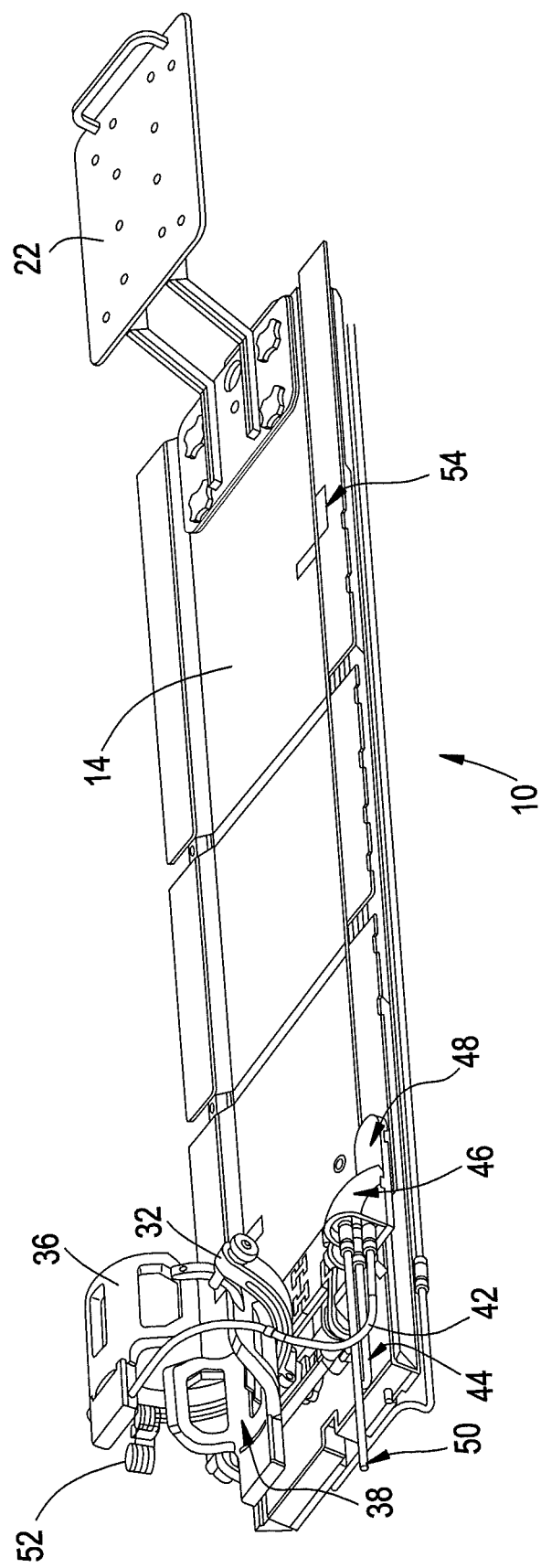
FIG. 2 depicts a side perspective view of the portion of the patient table of FIG. 1 without the patient.
Figure 5:
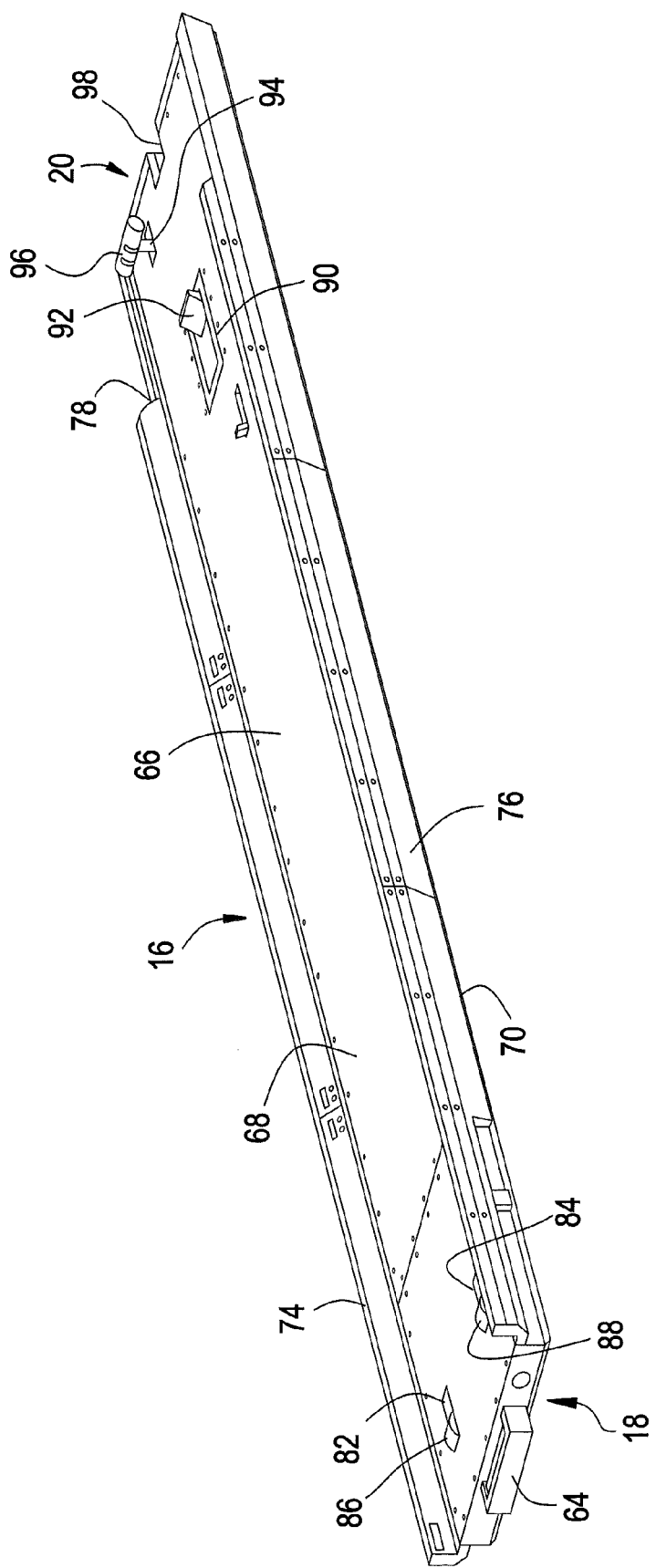
FIG. 5 shows a side perspective view of an exemplary embodiment of the cradle for use with the patient table of FIG. 1.
Figure 8:
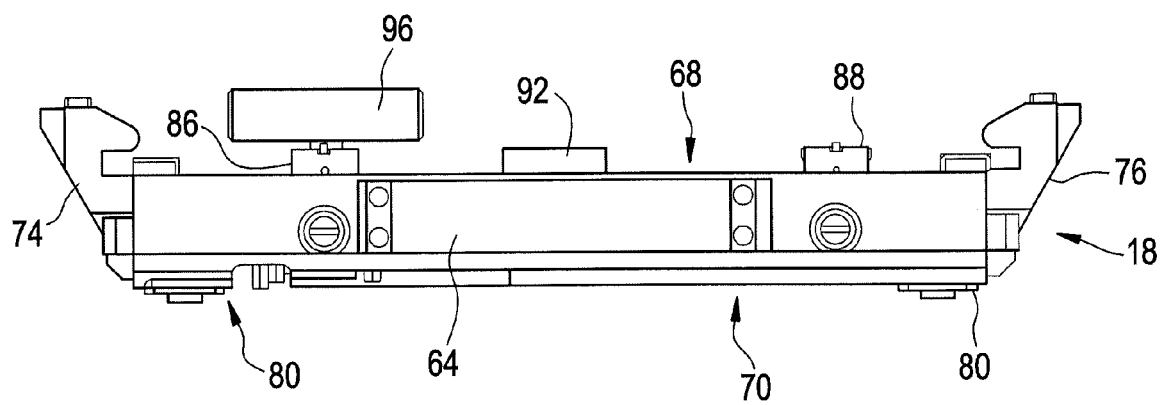
FIG. 8 shows an end plan view of a first end of the cradle of FIG. 5.

FIG. 2 shows the same patient table as in FIG. 1 except without the patient 12. The navigation arm 52 allows for the ability to attach a surgical navigation/tracking device (such as, but not limited to, DRF (optical), EM Transmitter, etc.) to the skull clamp 32 for use with surgical procedures. A patient grounding strip 54 is part of the transfer board 14 and used to ground the patient 12 to the surgical table 10, as specified by the applicable regulatory requirements for surgical tables.

The transfer board 14 is shown on its own in FIGS. 3 and 4. The patient grounding strip 54 is located near both ends 18, 20 of the transfer board 14. Attachment areas 56 are provided on the transfer board 14 near the ends 18, 20 for attaching the monitor plate 22 and the clamp 32 and RF coil 34 thereto, respectively. It should be understood that attachment of the monitor plate 22 and the clamp 32 and RF coil 34 to the attachment areas 56 may be accomplished by any known attachment devices that do not interfere with surgical or imaging procedures. As more clearly shown in FIG. 4, the transfer board 14 includes a top surface 58 for receiving a patient thereon, and a bottom surface 60 for resting upon the cradle 16. When the transfer board 14 is moved onto the cradle 16 of the table 10, roller receiving portions 62, provided adjacent the side portions 40 and extending from the first end 18 to the second end 20, slide along rollers 72 (FIG. 6) provided on the cradle 16. In the illustrated embodiment, roller receiving portions 62 include a curved, generally C-shaped wall extending from the bottom surface 60 to the top surface 58, although roller receiving portions 62 may have alternate designs for sliding along the rollers 72.

Turning to FIGS. 5-9, the cradle 16 is shown without the transfer board 14 positioned on top. The cradle 16 includes a top surface 68 for receiving the transfer board 14 and a bottom surface 70 for moving into an imaging system 500 (FIG. 25), such as an MRI bore, or seating upon the cradle supporting member 282 (FIG. 21) of the patient table 10. The top surface 68 includes a cover 66 which hides several mechanical elements, as will be further described below. The cover 66 may include a solitary cover, or may include two or more sectional pieces that together form the cover 66. In the illustrated embodiment, the cover 66 includes three sections. A first cover section 65 covers an area of the cradle 16 adjacent the first end 18, a second cover section 67 covers a middle area of the cradle 16, and a third cover section 69 covers an area of the cradle 16 relating to a third aperture 90 within the cover 66, as will be further described below. Other arrangements of covers would also be within the scope of these embodiments. The cover 66 may be removable from the cradle 16 for testing, repairing, replacing, or otherwise servicing any internal elements of the cradle 16. By using separate cover sections, individual sections, such as cover sections 65, 67, and 69 may be removed individually as required. The first end 18 of the cradle 16 includes a cradle emergency release handle 64. In the event of an emergency, when the cradle 16, transfer board 14, and patient 12 are positioned within an imaging system 500, such as an MRI bore, the cradle emergency release handle 64 can be pulled manually for moving the cradle 16, transfer board 14, and patient 12 out of the imaging system 500 more quickly than allowing the motorized system of the imaging system 500 to roll out the cradle 16 and transfer board 14 out of the imaging system 500. The cradle 16 and transfer board 14 are movable into and out of the imaging system 500 via casters 80 positioned on a bottom surface 70 of the cradle 16.

The cradle 16 further includes a first side 74 and a second side 76, which connect the first end 18 to the second end 20. A line of transfer board receiving rollers 72 is provided on each side 74, 76 of the cradle 16 for accepting the transfer board 14 onto the top surface 68 of the cradle 16. The roller receiving portions 62 surround the rollers 72 and slide along the rollers 72 as the transfer board 14 is moved onto the cradle 16. The line of rollers 72 ends at point 78 on each side 74, 76 prior to reaching the end 20 of the cradle 16. When the transfer board 14 is completely in place upon the cradle 16, the point 78 corresponds to a location where the clamp 32 and coil 34 are attached to the transfer board 14.

The cover 66 of the cradle 16 includes first and second apertures 82, 84 adjacent the first end 18 for allowing a first locker 86 (left hand locker) and a second locker 88 (right hand locker) within the cradle 16 to move into and out of engagement with the transfer board 14. The first locker 86 and second locker 88 engage with the transfer board 14 to hold it in place upon the cradle 16 until they are released.

The cover 66 further includes a third aperture 90 revealing a flipper 92, and a fourth aperture 94 for allowing a first locker manual release handle 96 to pass therethrough, both as will be further described below. The cradle 16 further includes a hook receiving indentation 98 for which a hook, or other grabbing protrusion, from the imaging system 500 can grab onto the cradle 16 and either move the cradle 16 into the imaging system 500, or secure it therein. As will also be further described below, pulling on the cradle emergency release handle 64 disengages the hook of the imaging system 500 from the hook receiving indentation 98 of the cradle 16, allowing the cradle 16, and thus the transfer board 14 and patient 12, to be removed from the imaging system 500.

Figure 9:
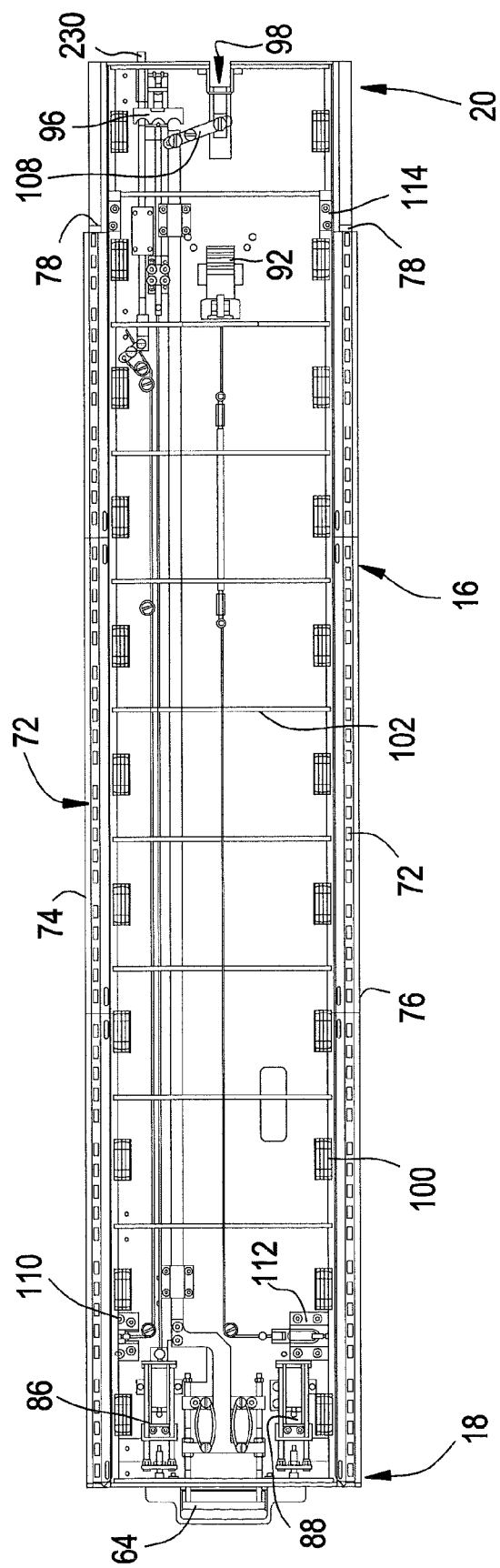
FIG. 9 shows a top plan view of the cradle of FIG. 5 with a cradle cover removed.
Figure 10:
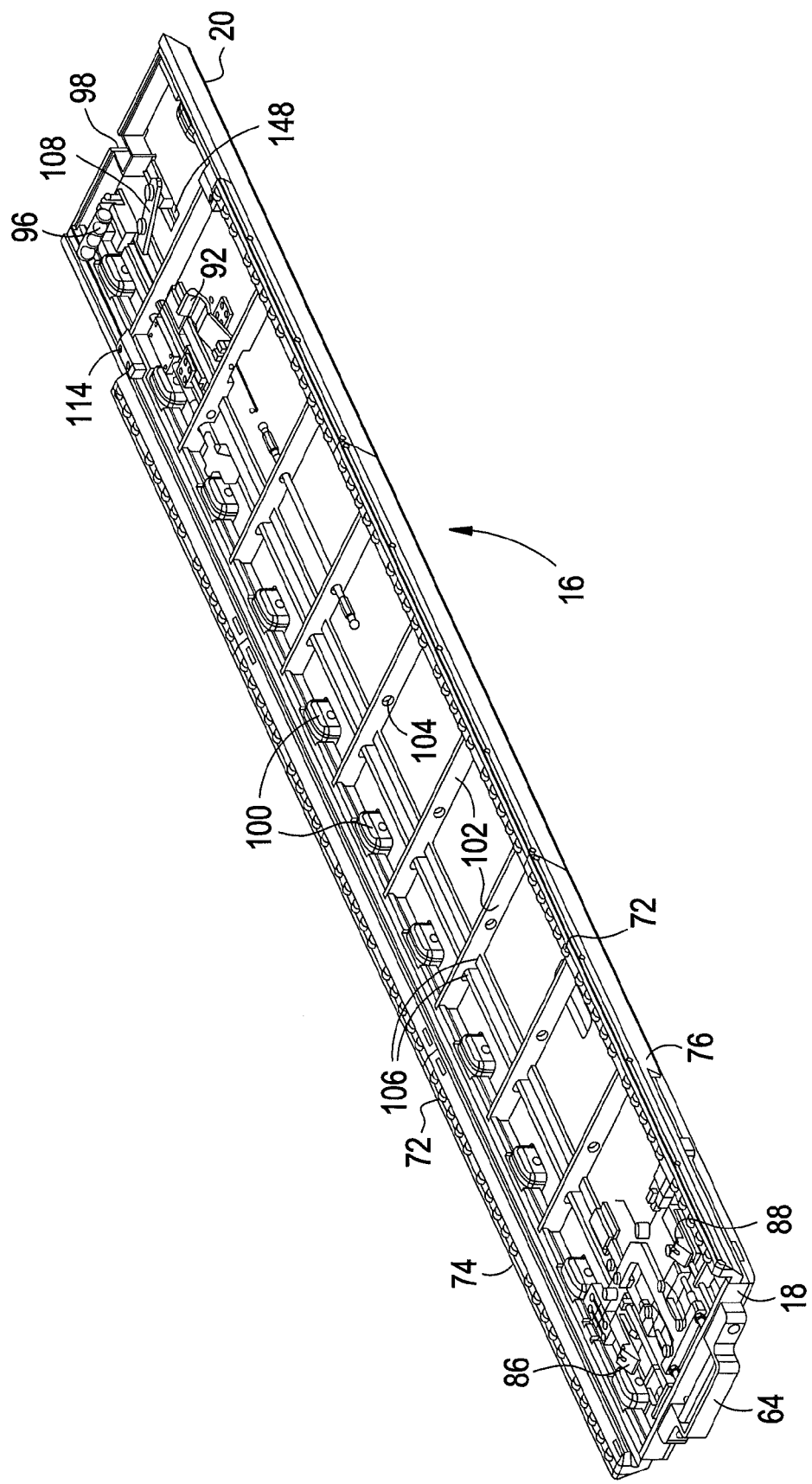
FIG. 10 shows a side perspective view of the cradle of FIG. 9 with the cradle cover removed.

FIGS. 9 and 10 show the cradle 16 with the cover 66, and all of its cover sections 65, 67, and 69 removed, thus revealing internal components of the cradle 16. Roller housings 100 are spaced apart from the first end 18 to the second end 20 and receive casters 80 therein. Support beams 102 are also spaced apart from the first end 18 to the second end 20. Support beams 102 connect the first side 74 to the second side 76, thus providing structural support for the cradle 16. The support beams 102 include apertures 104 and grooves 106 for allowing mechanical components to pass through where necessary.

Another component within the cradle 16 that is revealed with the cover 66 removed, and which will be further described below, is an emergency release mechanism 108, which includes a movable pull portion 118 associated with the cradle emergency release handle 64, for pushing a hook or other grabbing element of the imaging system 500 out of the hook receiving indentation 98. Also revealed is the first stopper 110 (left hand stopper) and the second stopper 112 (right hand stopper). When both stoppers 110 and 112 are released, the cradle 16 is allowed to move into and out of the imaging system 500. As will be further described below, stopper 110 is released when the first end 230 of block moving rod 228 is pushed by a low profile carriage assembly when the low profile carriage assembly is at the full out position and its hook is engaged with the receiving indentation 98. Part 114 serves as a positive stop for the transfer board 14. That is, when the transfer board 14 is rolled onto the cradle 16, a portion of the front face of the transfer board 14 encounters the part 114 and cannot move further past it. That is, the part 114 is a physical stop that extends slightly upward to abut with the transfer board 14. Thus, the transfer board 14 cannot be rolled off the second end 20 of the cradle 16.

Figure 11:
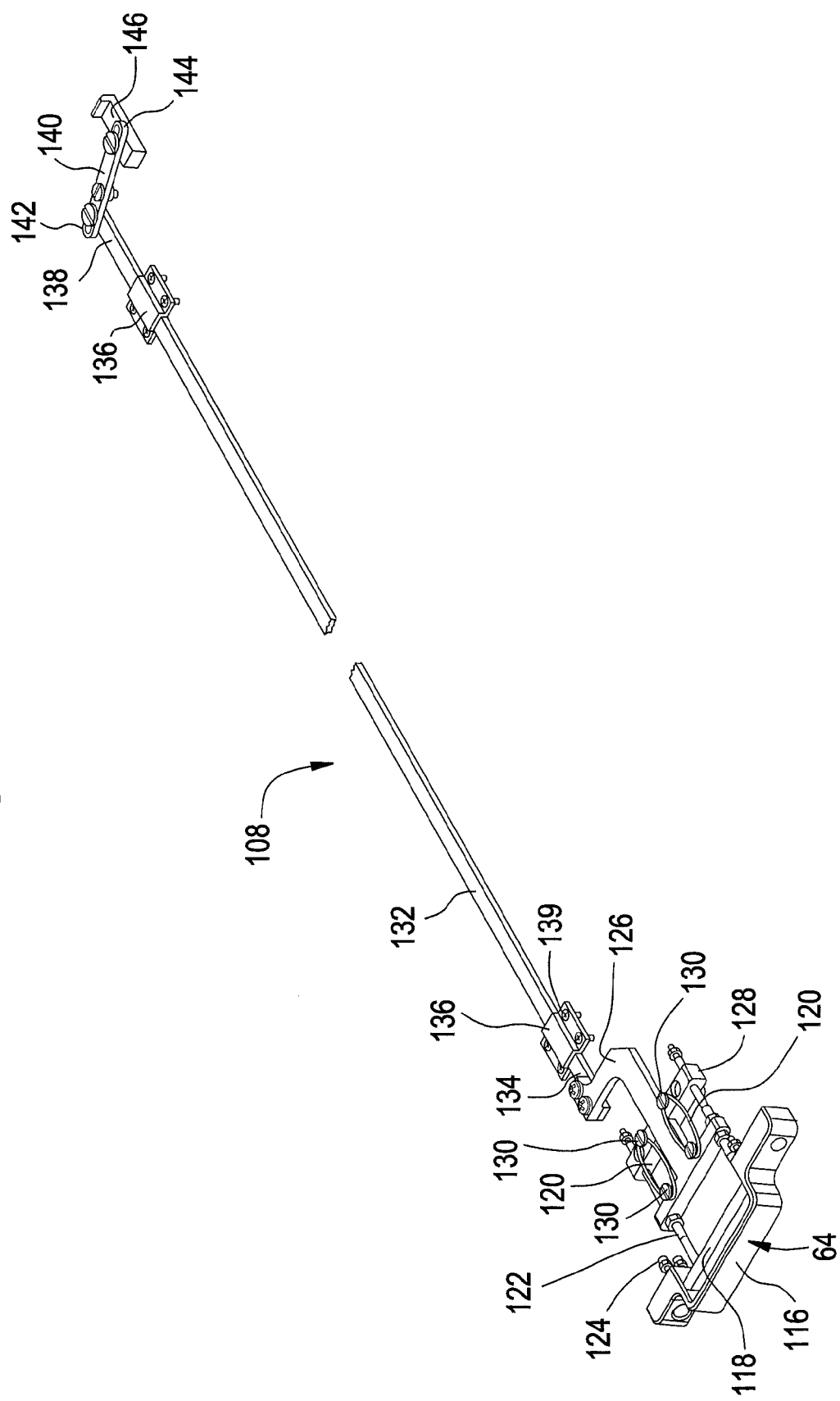
FIG. 11 shows a side perspective view of an exemplary hook release mechanism for use with the table of FIG. 1.

Turning now to FIG. 11, a detail of an exemplary emergency hook release mechanism 108 is shown. The emergency hook release mechanism 108 includes the cradle emergency release handle 64. The handle 64 includes a stationary U-shaped portion 116 that is affixed to the first end 18 of the cradle 16 using screws 124 or other suitable attachment device. The handle 64 further includes a movable pull portion 118 that is biased by O-rings 120 towards the O-ring supporter 128. The movable pull portion 118 is attached to link rods 122 that are attached for movement with a link beam 126. The link rods 122 move slidably within fixed O-ring supporter 128. The O-ring supporter 128 is fixed in location within the cradle 16 and includes a pair of O-ring holders 130. The link beam 126 also includes a pair of O-ring holders 130, and the O-rings 120 are stretched between a pair of O-ring holders 130, with one O-ring holder from each of the link beam 126 and the O-ring supporter 128. The movable link beam 126 is attached to a first end 134 of a movable link bar 132, which is partially shown within FIG. 11 and which extends a majority of the length of the cradle 16. The link bar 132 is movable within link bar guides 136 that are fixed within the cradle 16 using screws 139, or the like. A second end 138 of the link bar 132 is attached to pivotal linkage 140. Pivotal linkage 140 includes a first end 142 attached to the second end 138 of link bar 132 and a second end 144 attached to a slidable cammed hook pusher 146 that is slidable within a slot 148 in the bottom surface 70 of the cradle 16.

In operation, when the cradle 16, transfer board 14, and patient 12 need to be pulled quickly out of an imaging system 500, the handle 64 is grasped and the pull portion 118 is squeezed towards the stationary portion 116 which moves the link rods 122, and thus the link beam 126 and the link bar 132, in a direction towards the first end 18. The pivotal linkage 140 pivots such that a slotted groove within the second end 144 allows a connection between the second end 144 and the slidable cammed hook pusher 146 to move the slidable cammed hook pusher 146 towards the second end 20 of the cradle 16. The slidable cammed hook pusher 146 is moved into the hook receiving indentation 98 to push and release the hook of the imaging system 500 from the cradle 16. Once the hook is released, the handle 64 can continue to be pulled in a direction away from the imaging system 500 thereby removing the cradle 16 from the imaging system 500. When the handle 64 is released, the O-rings 120 pull the link beam 126 towards second end 20, and thus the link rods 122 and the pull portion 118 back away from the stationary portion 116. Through the link bar 132 and the linkage 140, the hook pusher 146 is pulled back in the slot 148 away from the second end 20, and thus reset for the next time the cradle emergency release handle 64 needs to be used.

While the illustrated embodiment shown in FIG. 11 has been described for use as the emergency release mechanism 108, it should be understood that the emergency release mechanism 108 may include alternate elements for releasing the hook or other cradle grabbing member from the imaging system 500 and remove the cradle 16 from the imaging system 500.

FIGS. 12 and 13 each show a partial view of the first locker 86 that includes a locking portion 148, shown in FIG. 12, and the first locker manual release handle 96, shown in FIG. 13. The first locker manual release handle 96 and the locking portion 148 are connected by line 150. Line 150 may be a cable, cording, rod, etc. A first end 152 of the line 150 is connected to a spring tab 164 in the locking portion 148 and a second end 154 of the line 150 is connected to a second end 158 of the slide rod 156 of the first locker manual release handle 96.

When the transfer board 14 is moved onto the cradle 16, it rolls over the locking portion 148, utilizing roller 163 of the first locker 86 in a direction from the first end 18 to the second end 20, as clearly demonstrated by arrow X. A first notch or groove within the lower surface 60 of the transfer board 14 slides over an angled surface 160 of a spring tab 164 and depresses the spring tab 164, forcing it downwardly towards the lower surface 70 of the cradle 16, until the notch or groove is over the tip 162, allowing the spring tab 164 to bias itself back upwardly and into the notch or groove. The spring tab 164 has a generally U-shaped cross-section as shown for providing the spring force. The tip 162 can include a roller 163 for allowing the transfer board 14 to roll smoothly over the tip 162. Once the tip 162 is within the notch or groove of the transfer board 14, the transfer board 14 is prevented from moving back in the direction from the second end 20 to the first end 18, demonstrated by arrow Y, because of the flat sided surface 166 provided on the other side of the tip 162.

FIG. 13 shows the first locker manual release handle 96 including a handle portion 168 that may be ergonomically designed with finger grooves as shown, or also could be implemented via a lever or other handle design/shape. The handle portion 168 is attached to a connecting rod 170 that moves within a slot 172 in a fixed handle support 174 secured within the cradle 16. When the handle 168 is pulled, the slide rod 156 is pulled in the direction X. The slide rod 156 is slidable within slide rod guide 176. Movement of the slide rod 156 in the direction X also pulls the line 150 in the direction X. The first end 152 of the line 150 is attached to the end 178 of the angled surface 160. Thus, pulling the line 150 in the direction X pulls the end 178 of the spring tab 164 downwardly, thus allowing the transfer board 14 to move back in the direction Y, and off of the cradle 16.

While a specific mechanical arrangement has been described for the first locker 86, it should be noted that alternate arrangements for a first locker 86 may also be devised that includes a system for preventing the transfer board 14 from moving off of the cradle 16 and a manual release for disengaging the system.

Figure 14:
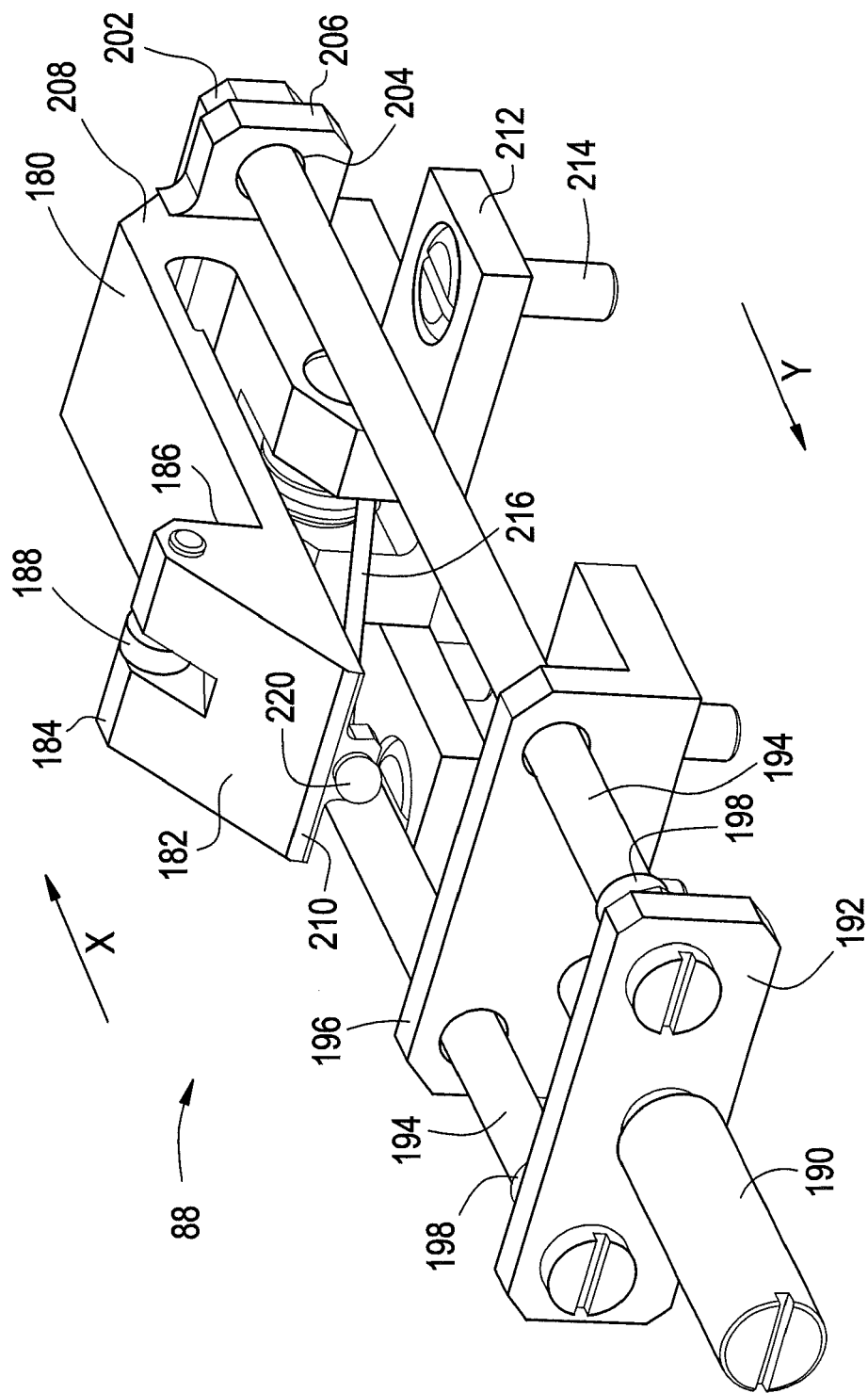
FIG. 14 shows a first side perspective view of an exemplary embodiment of a second locker for use with the table of FIG. 1.
Figure 15:
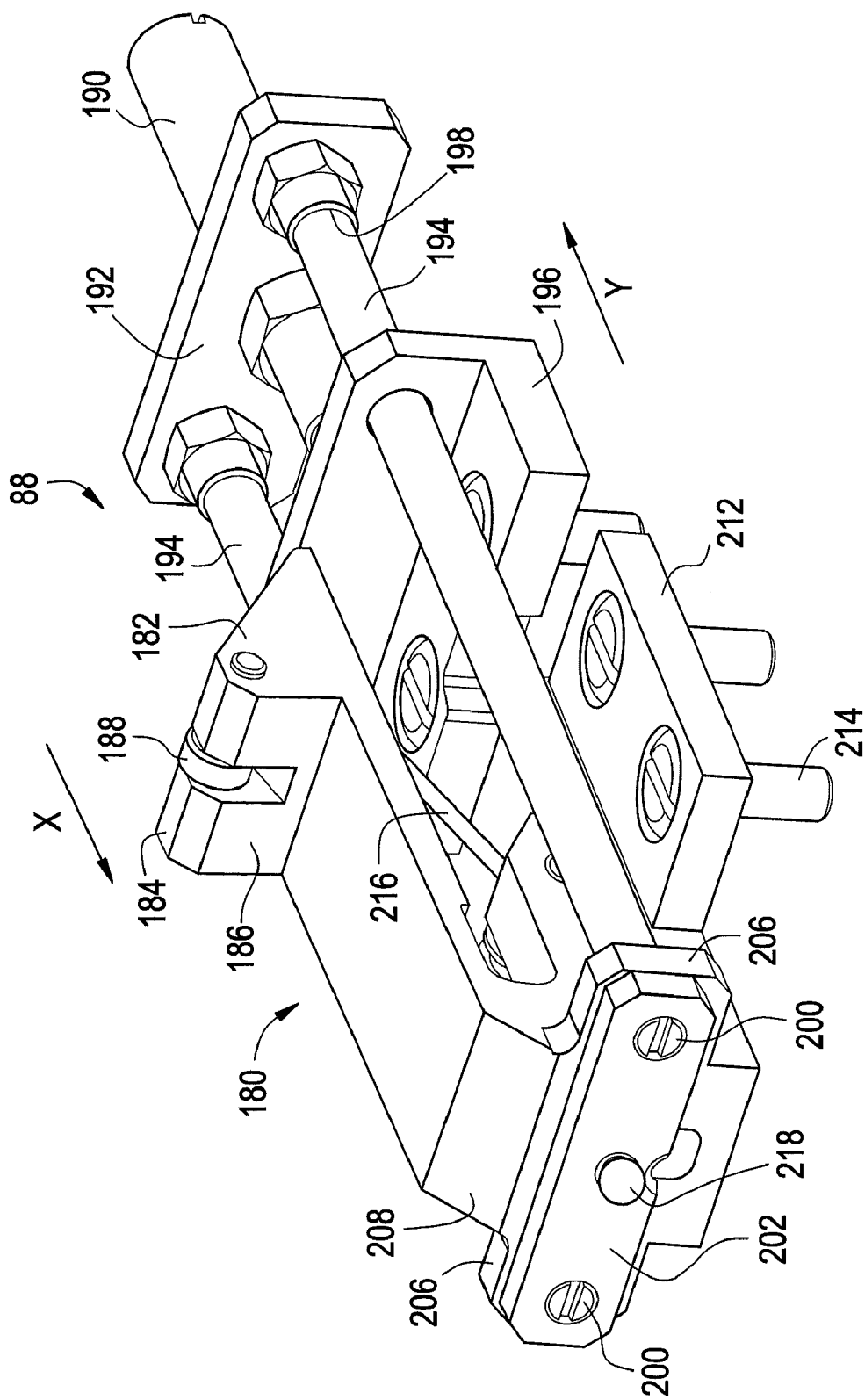
FIG. 15 shows a second side perspective view of the second locker of FIG. 14.

FIGS. 14 and 15 show altering side perspective views of the second locker 88. The second locker 88, as with the first locker 86, serves to secure the transfer board 14 in place on the cradle 16 and includes a spring tab 180 similar to the spring tab 164. As the transfer board 14 is moved in the direction X over the angled surface 182 of the spring tab 180, the spring tab 180 is depressed, forcing it downwardly, until a second notch or groove in the lower surface 60 of the transfer board 14 is over a tip 184, allowing the spring tab 180 to bias itself back upwardly and into the second notch or groove. The tip 184 can include a roller 188 for allowing the transfer board 14 to roll smoothly over the tip 184. The spring tab 180 has a generally U-shaped cross-section as shown for providing the spring force. Once the tip 184 is within the notch or groove of the transfer board 14, the transfer board 14 is prevented from moving back in the direction from the second end 20 to the first end 18, demonstrated by arrow Y, because of the flat sided surface provided on the other side of the tip 184.

The second locker 88 does not include a manual release handle, as does the first locker 86. Instead, the second locker 88 is released when the table 10 is docked with a second complimentary table, such as table 400 shown in FIG. 25. The second table 400, also formed to receive the transfer board 14, includes either an surface or a protrusion that is engageable with the pusher knob 190. The pusher knob 190 may either protrude out of the first end 18 of the cradle 16, or, alternatively, the first end 18 of the cradle 16 may include an opening for receiving a protrusion from the second table 400. In any case, when the table 10 is docked with the second table 400, or other compatible table, the pusher knob 190 is pushed in the direction X, which in turn pushes a first movable platform 192 and the attached pusher rods 194. The pusher rods 194 are slidable through the rod guide 196 that is fixed within the cradle 16. A first end 198 of each of the pusher rods 194 is attached to the first movable platform 192. A second end 200 of each of the pusher rods 194 is attached to a second movable platform 202. The pusher rods 194 are also slidable through openings 204 provided in extensions 206 protruding from a second end 208 of the spring tab 180, opposite the first end 210 of the spring tab 180. The second end 208 is fixedly held within the cradle 16 by a spring tab support 212 via securement devices 214 such as, but not limited to, screws, bolts, rivets, etc.

A line 216, such as, but not limited to, a cable, cording, rod, etc. is attached at a first end 218 to the second movable platform 202 and a second end 220 to the end 210 of the spring tab 180. When the pusher knob 190 is pushed in the X direction by a complimentary table abutting with table 10, the first movable platform 192 moves the pusher rods 194 and thus the second movable platform 202 in the X direction. Movement of the second movable platform 202 in the X direction causes the line 216 to be pulled in the X direction, thus causing the end 210 to be pulled downwardly towards the bottom surface 70 of the cradle 16, thus pulling the tip 184 out of the second notch or groove and allowing the transfer board 14 to move back in the direction Y, and off of the cradle 16.

While a specific mechanical arrangement has been described for the second locker 88, it should be noted that alternate arrangements for the second locker 88 may also be devised that includes a system for preventing the transfer board 14 from moving off of the cradle 16 until the table 10 is engaged with a complimentary table.

The first and second lockers 86, 88 may also be deemed vertical interlocks as they operate to keep the transfer board 14 from moving off the cradle 16 until cleared and they activate by moving a locking portion (e.g., the tips 162, 184 of the spring tabs 164, 180, respectively) vertically, that is, towards and away from the top surface 68 and bottom surface 70 of the cradle 16.

FIGS. 16 and 17 show enlarged partial views of the first stopper 110. When the first stopper 110 is released, the cradle 16 is allowed to move into and out of the imaging system 500 only if the transfer board 14 is fully on the cradle 16 thereby activating the second stopper 112. The first stopper 110 may be activated by the low profile carriage assembly ("LPCA") on the front of the imaging system 500, where the imaging system 500 may be an MRI system. The cradle 16 includes a mechanical interlock/rod within the first stopper 110 that is depressed when the table 10 is connected to the imaging system 500. This effectively serves as a way to "communicate" with the table 10, so the table 10 "knows" it is connected to the imaging system 500.

The first stopper 110, as can be seen in FIG. 16, is situated adjacent the side 74 of the cradle 16. The first stopper 110 includes a slidable block 220 that is movable with respect to a fixed block support 222 fixed with respect to the cradle 16 via screws or other securement devices inserted within apertures 224 within the fixed block support 222. The slidable block 220 can be biased in an outwardly projecting position, such as shown in FIG. 16, by the O-ring 226. In this outwardly projecting position, the block 220 is located within a first groove in the cradle accepting portion/cradle receiving member 282 (FIG. 21) of the table 10.

When the table 10 is moved into position with the imaging system 500, the block moving rod 228, as shown in FIG. 17, is moved in the Y direction as shown. The block moving rod 228 includes a first end 230 that protrudes outwardly from the second end 20 of the cradle 16. A larger diametered portion 232 is provided adjacent the first end 230 for preventing the rod 228 from protruding too much from the second end 20. The block moving rod 228 is slidable within a block moving rod guide 242. The second end 234 of the block moving rod 228 is attached to a connector 236 for connecting the second end 234 of the block moving rod 228 to a line pulling linkage 238 connected to the connector 236 by a securement device 240. The line pulling linkage 238 is connected at end 244 to a first end 248 of a line 246 shown partially in FIG. 17. As shown in FIG. 16, a second end 250 of the line 246 is connected to the slidable block 220.

Thus, when the block moving rod 228 is moved in the Y direction, the line 246 between a line support 252 provided adjacent the line pulling linkage 238 and a line support 254 provided adjacent the block support 222 is pulled in the X direction. When the line 246 is pulled, the second end 250 of the line 246 pulls the slidable block 220 in a direction from the first side 74 to the second side 76 of the cradle 16 and into the block support 222, thus removing the block 220 as an obstruction of movement from the cradle accepting portion of the table 10. When the table 10 is not in engagement with the imaging system 500, then the O-ring 226 moves back into its biased condition and moves the block 220 back outwardly as shown in FIG. 16, and pulls the line 246 in the Y direction, thus pushing the block moving rod 228 in the X direction, and pushing the first end 230 of the block moving rod 228 back out the second end 220.

While a specific mechanical arrangement has been described for the first stopper 110, it should be noted that alternate arrangements for the first stopper 110 may also be devised that includes a system for preventing the cradle 16 from moving off of the cradle supporting portion 282 of the table 10 until the table 10 is engaged with the imaging system 500, or other complimentary system.

FIGS. 18-19 show enlarged partial views of the second stopper 112. The second stopper 112, as can be seen in FIG. 18, is situated adjacent the side 76 of the cradle 16. The second stopper 112 includes a slidable block 258 that is movable with respect to fixed block support 260 fixed with respect to the cradle 16 via screws or other securement devices 262. The slidable block 258 can be biased in an outwardly projecting position, such as shown in FIG. 18. In this outwardly projection position, the block 258 is located with a second groove in the cradle accepting portion of the table 10, as will be further described below.

When the transfer board 14 is moved into position over flipper 92 that is revealed through aperture 90 in the cover 66, the lower surface 60 of the transfer board 14 pushes the first end 264 downwardly, towards the lower surface 70 of the cradle 16. The second end 266 of the flipper 92 is attached to a line 268. As the flipper 92 is levered over flipper support 270, the second end 266 moves upwardly, towards a top surface 68 of the cradle 16. As the second end 266 moves upwardly, the line 268 is pulled in the X direction, thus pulling linkage 272 and line 274 in the X direction. A block pulling end 276 of the line 274 pulls the slidable block 258 within the block support 260 as the line 274 is pulled around the line support 278. Thus, the block 258 is removed as an obstruction of movement from the cradle accepting portion 282 of the table 10. When the transfer board 14 is not in position upon the cradle 16, the flipper 92 is biased to the condition where the end 264 protrudes from the aperture 90 and the block 258 protrudes outwardly from the block support 260 for engagement with the second groove of the cradle accepting portion 282 of the table 10.

While a specific mechanical arrangement has been described for the second stopper 112, it should be noted that alternate arrangements for the second stopper 112 may also be devised that includes a system for preventing the cradle 16 from moving off of the cradle supporting portion 282 of the table 10 until the transfer board 14 is completely in position on cradle 16.

The first and second stoppers 110, 112 may also be deemed horizontal interlocks, as they prevent the cradle 16 from moving off of the table 10 until cleared, and they activate by moving slidable blocks 220, 258 horizontally, that is, towards and away from the first side 74 and the second side 76 of the cradle 16, and generally parallel with top and bottom surfaces 68, 70 of the cradle 16.

Figure 21:
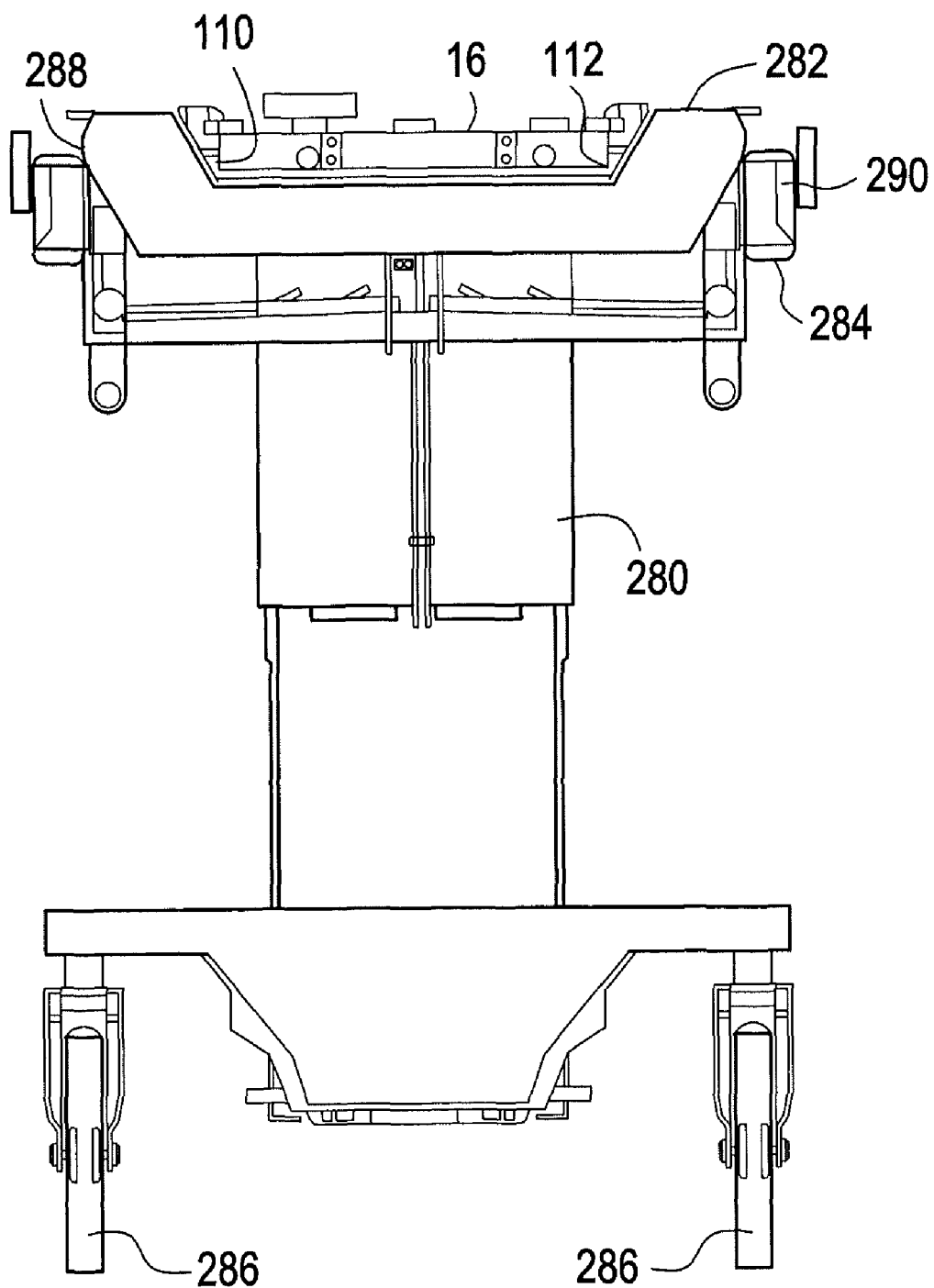
FIG. 21 shows an end view of the patient table of FIG. 20.

FIGS. 20-21 show the remainder of the table 10, including the main support 280, the cradle accepting portion 282, and a docking assembly 284 for docking with a complimentary second table 400. The docking assembly 284 is positioned on the first end 18 of the table 10. The table 10 also includes pivotal wheels 286 for moving the table 10 into position with the complimentary table 400, an imaging system 500, or other table or imaging system.

FIG. 21 further shows a cradle 16 positioned within the cradle accepting portion 282 of the table 10. First and second stoppers 110, 112 are shown with their slidable blocks 220, 258 engaged with grooves 288, 290, respectively, within the cradle accepting portion 282.

Figure 22:
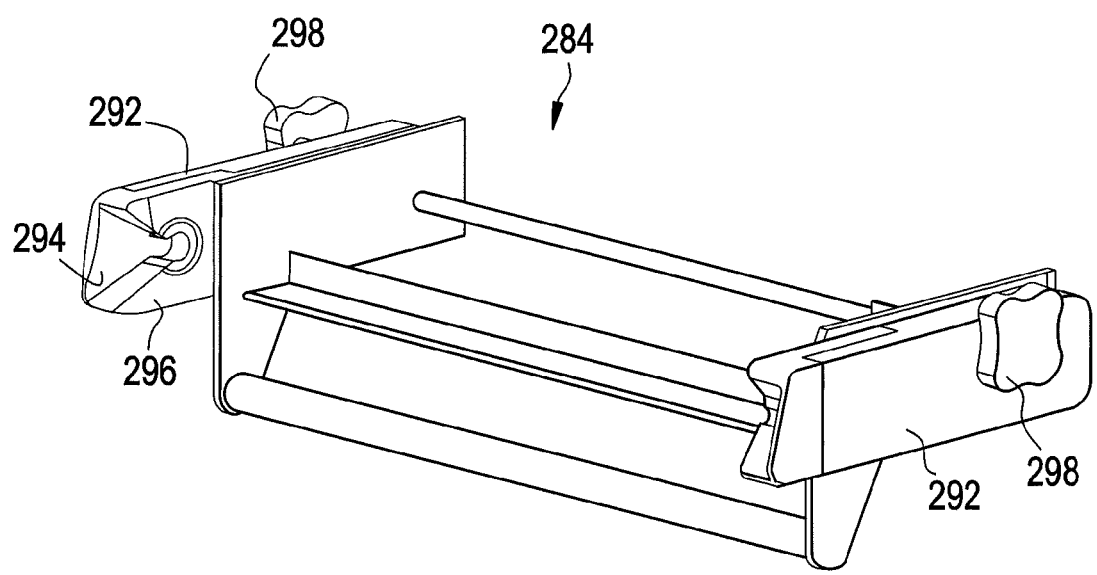
FIG. 22 shows a side perspective view of an exemplary embodiment of a docking assembly attached to first end of the table of FIG. 20.

The docking assembly 284 positioned on the first end 18 of the table 10 is shown on its own within FIG. 22. The docking assembly 284 is used for docking the patient table 10 with the manual table 400, such as a Transmobile table 400, and includes a pair of spaced table engaging bodies 292 that flank the sides of the table 10. The docking assembly 284 is designed to accept horizontally protruding pins 402 from a table 400 to be engaged. Each table engaging body 292 includes a tapered pin receiving channel 294. The pin 402 from each side of the table 400 engaging with table 10 is easily received within the widest portion of the channel 294 and is guided by the tapering walls of the channel 294 until each pin 402 is seated with a center of a movable pin locking device 296. Once the pins 402 are seated with the pin locking devices 296, pin locking knobs 298 can be rotated to rotate the C-shaped locking device 296 such that the opening of the C-shaped locking device 296 no longer faces the channel 294. Thus, the pins 402 and therefore the table 400 cannot be removed from the docking assembly 284 until the pin locking knob 298 is rotated to rotate the opening of the C-shaped locking device 296 back in line with the channel 294.

This system enables the possibility for 1.5 T and/or 3.0 T MRI scans during surgical procedures. Smooth patient transfer is possible from a table 400, such as a VIWAS table system, at any time during a surgical procedure. The surgical suite is fully equipped and can remain independent of the imaging suite, while the imaging suite remains independent to perform clinical scans of regular patients. While the illustrated embodiments are shown designed for neurosurgery, other surgical procedures are also possible. The patient table 10 has multi-connectivity capability and can interface with other equipment such as, but not limited to, the Alpha Maquet 1150 surgical table and Maquet Transmobile both by Maquet.

Figure 23:
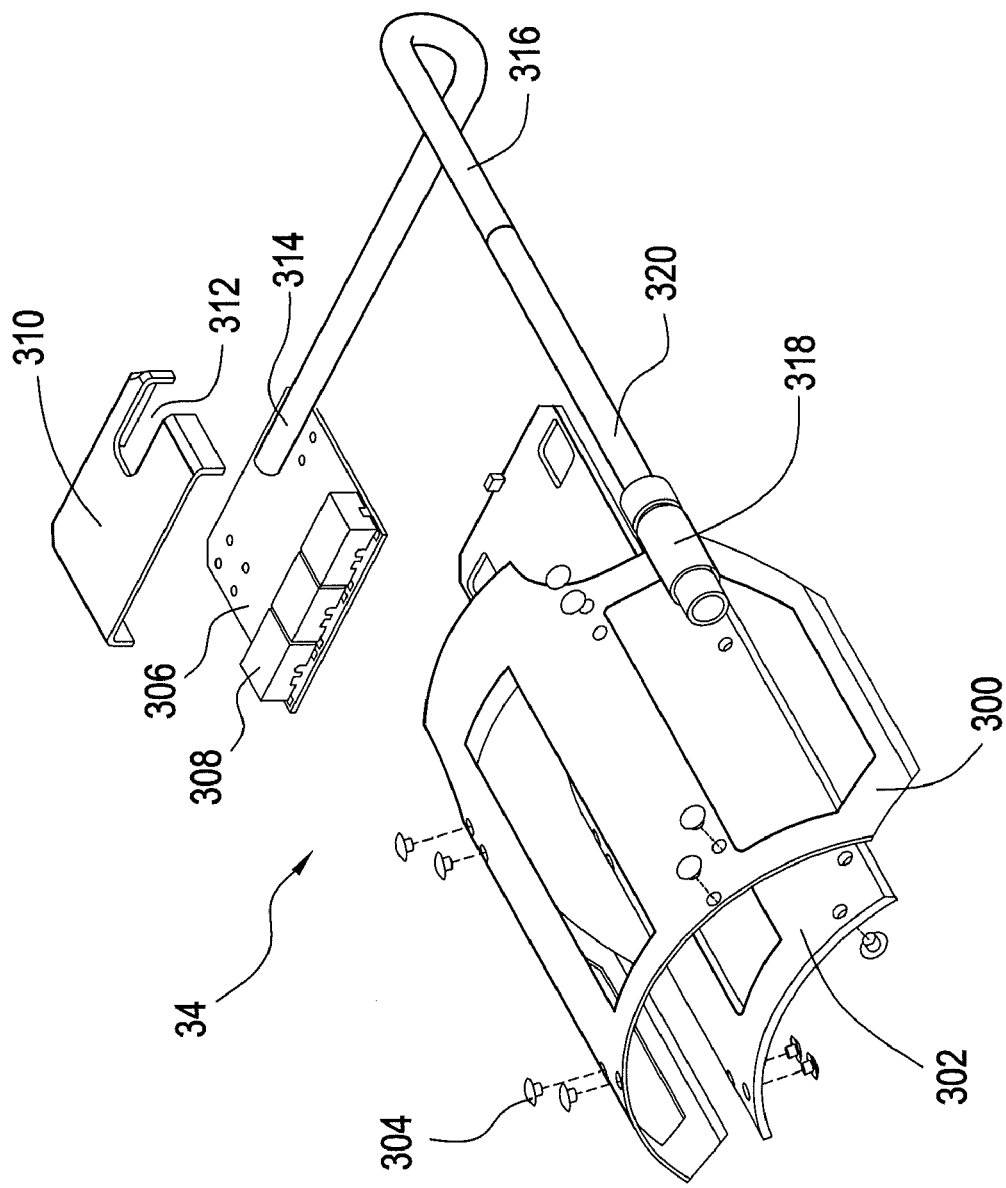
FIG. 23 shows an exploded perspective view of an exemplary embodiment of an RF coil for use with the table of FIG. 1.
Figure 24:
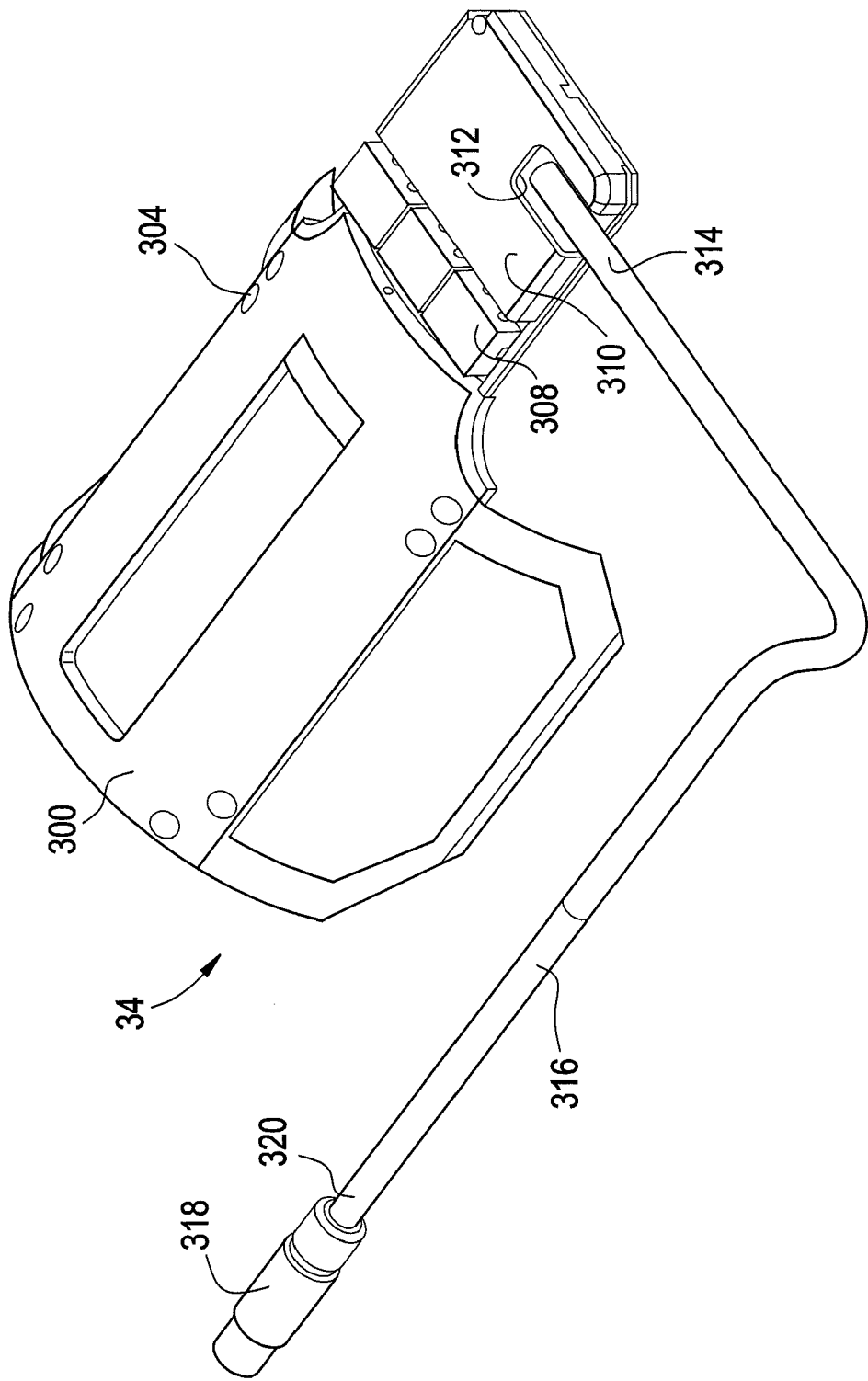
FIG. 24 shows a side perspective view of the assembled RF coil of FIG. 23.

Use of the dedicated RF coil 34 in this configuration enables (helps ensure) maximum SNR and improved image quality while also providing maximum flexibility in the clinical application to accommodate multiple patient positionings and procedures. The RF coil 34 is shown in FIGS. 23 and 24. The RF coil 34 includes a flexed printed circuit board ("PCB") 300 attached to a backing 302 by rivets 304, or other suitable fasteners. The backing 302 is attached to an input PCB 306 which supports RF traps 308. The input PCB 306 is protected by protection frame 310. The protection frame 310 includes a window 312 through which a first end 314 of a coil cable 316 extends. The coil cable 316 can be either the coil cable 42 or 44, or other coil cable for a coil designed for a different anatomical part. A second end 320 of the coil cable 316 includes a coil connector 318 for easily connecting to the intermediate box 46.

For MR compatibility, the surgical table may be made from materials that are radiolucent. In one embodiment, the table implements a fiber composite material that is MR and Xray translucent and can be used in conjunction with a compatible surgical table and patient transporter.

As shown generally in FIG. 25, the MRI compatible surgical patient table 10 and cradle 16 with docking assembly 284 includes the surgical cradle 16 to accept the transfer board 14 and contains unique internal safety interlocks and the physical materials for imaging transparency to permit proper MR scanner function with an imaging system 500. The docking assembly 284 integrated with the first end 18 of the surgical table 10 allows proper docking with a complimentary table 400, such as the Maquet transmobile and VIWAS. The cradle 16 has special interlocks that only release the transfer board 14 and patient 12 when docked with the complimentary equipment. The complimentary table 400 contains similar interlock pin releases, that is, it requires mechanism locking before patient transfer.

While FIG. 25 show the table 400 separated from the table 10 and the table 10 separated from the imaging system 500, it should be understood that the table 400 and the table 10 are movable bodies that may be movable relative to each other and the imaging system 500. For example, the table 400 is movable towards and removably dockable with the table 10 for moving the transfer board 14 from the table 400 to the table 10. Similarly, the table 10 is movable towards and removably connectable to the imaging system 500 for moving the cradle 16 from the table 10 to within the imaging system 500. The floor 390 may include tracks for guiding wheels of the second table 400, thus quickly guiding the second table 400 into engagement with the patient table 10.

As described above, when the table 400 is docked with the table 10, a pin 402 from the table 400 is inserted within the channel and pin locking device 294, 296 of the docking assembly 284. Also, when the table 400 is completely docked with the table 10, pusher knob 190 of second locker 88 is engaged by the end of the table 400 (or a protrusion extending therefrom) to disengage the locker 88, thus allowing the transfer board 14 to move from the table 10 back to the table 400. When the table 10 is engaged with the imaging system 500, the first end 230 of block moving rod 228 of first stopper 110 is pressed inwardly into the cradle 16 thus slidably moving a block from between the cradle 16 and the cradle supporting member 282. Simultaneously, second stopper 112 is pressed inwardly into the cradle 16 when the transfer board 14 is fully located upon the cradle 16, thus allowing the cradle 16 to move into the imaging system 500. When the table 10 is positioned relative to the imaging system 500, the system cable 50, as shown in FIG. 1, from the RF coil 34 can be connected to the interface 502 of the imaging system 500. It should be understood that the interface 502 may be positioned anywhere relative to the imaging system 500, and is not limited to the illustrated location.

The cradle 16 is a unique adapter, which allows full functional use of the MRI scanner, or other imaging system, and transfers patients smoothly and safely. The cradle frame is a special flat bonded structure, designed and has been tested to withstand four times the maximum patient weight. The roller blades sections 72 are also structural and interlock with the cradle 16, and are removable in a matter of minutes. The docking assembly 284 permits safe transfer of the transfer board 14 with the complimentary patient transporter 400. Safety interlocks are included within the cradle 16 to permit safe, smooth patient transfer.

The dedicated RF coil 34 enables positioning the device close to the anatomy and can be placed between the skull clamp 32 and the anatomy to be imaged. The ability to use the coil 34 in this placement/location allows for maximum SNR for diagnostic imaging. The coil interface configuration enables the ability to connect the coil 34 to an intermediate connection location, e.g. intermediate box 46, which provides maximum flexibility in applications and procedures. The connection implementation can be attached to the transfer board 14 on the patient's left or right side and coil 34 enables the use of an anterior coil 36, a posterior coil 38, or both used in conjunction. This capability allows for increased user/application flexibility to accommodate the particular procedure and facilitates the use in procedure/workflow and moving the patient in/out of MR and connection to the MR system during surgical procedures.

In addition, while the invention has been described with reference to exemplary embodiments, it will be understood by those skilled in the art that various changes may be made and equivalents may be substituted for elements thereof without departing from the scope of the invention. Many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A patient imaging and transfer system, the system comprising:
    an imaging system;
    a patient table including a cradle supporting member, a second end of the patient table engageable with the imaging system;
    a cradle slidably received on the cradle supporting member and within the imaging system, the cradle movable between the patient table and the imaging system when the second end of the patient table is engaged with the imaging system;
    a second table, an end of the second table engageable with a first end of the patient table; and,
    a patient carrying board slidable between the second table and the cradle when the second table is engaged with the first end of the patient table;
    wherein a patient is transferable from the second table to the imaging system without removing the patient from the board.

2. The patient imaging and transfer system of claim 1 further comprising a coil for use with the imaging system, the coil attached relative to the board, a coil cable extending from the coil, an intermediate box attached to the board, and a system cable extending from the intermediate box, wherein the system cable is connectable to the imaging system.

3. The patient imaging and transfer system of claim 2 further comprising an anatomical clamp attached to the board, the coil configured to be positioned between the clamp and a patient.

4. The patient imaging and transfer system of claim 1 wherein the cradle includes a locker for preventing the board from sliding off the cradle when in a locked position and a stopper for preventing the cradle from sliding off the cradle supporting member when in an engaged position.

5. The patient imaging and transfer system of claim 4 wherein the locker includes a first locker and a second locker, the first locker including a locker manual release mechanism and the second locker automatically disengaging the board from the cradle when the first end of the patient table is docked with the second table and wherein the stopper includes a first stopper disengaging from the cradle supporting member when the second end of the patient table abuts the imaging system, and a second stopper disengaging from the cradle supporting member when the board is fully supported upon the cradle.

* * * * *